(12) United States Patent
Oden et al.

(10) Patent No.: US 10,945,777 B2
(45) Date of Patent: Mar. 16, 2021

(54) SURGICAL INSTRUMENT AND METHOD FOR PERFORMING AN ORTHOPAEDIC SURGICAL PROCEDURE

(71) Applicant: DEPUY IRELAND UNLIMITED COMPANY, County Cork (IE)

(72) Inventors: Jeremy Oden, Huntington, IN (US);
Steven Kitch, Warsaw, IN (US);
Graeme John Dutton, Burnley (GB);
Takayuki Nakamura, Saitama (JP);
Kevin Cooney, New Haven, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 147 days.

(21) Appl. No.: 16/369,443

(22) Filed: Mar. 29, 2019

(65) Prior Publication Data
US 2020/0305942 A1 Oct. 1, 2020

(51) Int. Cl.
*A61B 17/88* (2006.01)
*A61F 2/46* (2006.01)
*A61B 17/15* (2006.01)

(52) U.S. Cl.
CPC ........ *A61B 17/8866* (2013.01); *A61B 17/154* (2013.01); *A61F 2/461* (2013.01); *A61F 2002/4627* (2013.01)

(58) Field of Classification Search
CPC .............. A61B 17/8866; A61B 17/154; A61F 2002/4627
See application file for complete search history.

(56) References Cited

U.S. PATENT DOCUMENTS

| | | | |
|---|---|---|---|
| 1,920,821 A * | 8/1933 | Wassenaar | A61B 17/6408 606/86 R |
| 5,213,112 A | 5/1993 | Niwa et al. | |
| 5,540,696 A | 7/1996 | Booth, Jr. et al. | |
| 5,911,723 A * | 6/1999 | Ashby | A61B 17/154 606/88 |
| 5,944,723 A * | 8/1999 | Colleran | A61B 17/8866 606/208 |
| 6,022,377 A | 2/2000 | Nuelle et al. | |
| 7,156,853 B2 | 1/2007 | Muratsu | |
| 8,998,917 B2 | 4/2015 | Colquhoun et al. | |
| 9,050,197 B2 | 6/2015 | Lorio et al. | |
| 2002/0156480 A1* | 10/2002 | Overes | A61B 17/025 606/90 |
| 2014/0288563 A1 | 9/2014 | Claypool et al. | |
| 2016/0106409 A1 | 4/2016 | Moholkar | |

(Continued)

FOREIGN PATENT DOCUMENTS

| | | |
|---|---|---|
| CN | 204797805 U | 11/2015 |
| CN | 107693065 A | 2/2018 |

(Continued)

OTHER PUBLICATIONS

DePuy Orthopaedics, Inc., Knee Balancer, Complementing P.F.C. Sigma and LCS Complete EGF Instrumentation, Aiding in a Well-Balanced, Successful Total Knee Replacement, 16 pages.

(Continued)

*Primary Examiner* — Christian A Sevilla
(74) *Attorney, Agent, or Firm* — Barnes & Thornburg LLP

(57) ABSTRACT

Surgical instruments, systems, and methods of performing orthopaedic surgical procedures on a patient's knee are disclosed.

18 Claims, 14 Drawing Sheets

(56) References Cited

U.S. PATENT DOCUMENTS

2017/0119406 A1* 5/2017 Triplett ................. A61B 17/16
2019/0008501 A1   1/2019 Plaskos et al.
2019/0105092 A1* 4/2019 Castaneda .......... A61B 17/8866

FOREIGN PATENT DOCUMENTS

| EP | 0809969 A2 | 12/1997 |
| --- | --- | --- |
| GB | 2261604 A | 5/1993 |
| JP | 4095919 B2 | 6/2008 |
| JP | 4949874 B2 | 6/2012 |
| JP | 5642878 B2 | 12/2014 |
| JP | 5803013 B2 | 11/2015 |
| JP | 6303249 B2 | 4/2018 |
| WO | 2012020460 A1 | 2/2012 |
| WO | 2013013094 A1 | 1/2013 |

OTHER PUBLICATIONS

DePuy Orthopaedics, Inc., Hy-Flex II, Total Knee & Ligament Balancing System, Product Rationale, 1990s, 1 page.
Smith & Nephew, Journey II TKA, Total Knee System, Surgical Technique Addendum, Flexion/Extension Gap Balancing, 2017, 8 pages.
Zimmer FuZion Instruments, Surgical Technique (Beta Version), 2014, 52 pages.
Partial European Search Report, European Application No. PCT/EP2020/053959, dated Apr. 28, 2020, 17 pages.

* cited by examiner

SURGICAL INSTRUMENT AND METHOD FOR PERFORMING AN ORTHOPAEDIC SURGICAL PROCEDURE

CROSS REFERENCE

Cross reference is made to U.S. patent application Ser. No. 16/369,451 entitled "METHODS OF OPERATING A SURGICAL INSTRUMENT AND PERFORMING A SURGICAL PROCEDURE TO BALANCE A PATIENT'S KNEE" by Steven Kitch et al. which is assigned to the same assignee as the present application, filed concurrently herewith, and hereby incorporated by reference.

TECHNICAL FIELD

The present disclosure relates generally to methods and instruments for use in the performance of orthopaedic procedures such as knee replacement procedures.

BACKGROUND

In some orthopaedic surgical procedures, such as a total knee replacement procedure, ligament balancing devices (commonly known as ligament balancers) may be used to balance the surrounding soft tissue (i.e., ligaments) of a patient's joint. For example, in a total knee replacement procedure, ligament balancing may be performed to ensure a generally rectangular shaped extension gap and a generally rectangular shaped flexion gap at a predetermined joint force value between the patient's natural or prosthetic proximal tibia and the patient's natural or prosthetic distal femur. To do so, a ligament balancer may be used to measure the medial and lateral joint forces and the medial and lateral gap distances when the patient's leg is in extension (i.e., the patient's tibia is positioned at about 0 degrees relative to the patient's femur) and in flexion (i.e., the patient's tibia is positioned at about 90 degrees relative to the patient's femur). In either extension or flexion, if the medial and lateral gap distances are not approximately equal (i.e., do not form a generally rectangular shaped joint gap) at the predetermined joint force value, ligament release may be performed to equalize the medial and/or lateral gap distances. A typical ligament balancer includes manually operated mechanical mechanisms, such as springs, to determine the joint force and to adjust the extension/flexion gap distance.

SUMMARY

According to one aspect of the disclosure, an orthopaedic surgical instrument is disclosed. The orthopaedic surgical instrument comprises a first component including a passageway that extends along a longitudinal axis, and a first plate coupled to a superior end of the first component. The first plate is shaped to be positioned on a proximal end of a patient's tibia. The orthopaedic surgical instrument also comprises a second component including a shaft positioned in the passageway of the first component and an arm extending posteriorly from a superior end of the shaft. A second plate is pivotally coupled to a posterior end of the arm of the second component superior to the first plate. The second plate is configured to pivot about a pivot axis intersecting the longitudinal axis of the first component to tilt the second plate relative to the first plate. An inferior-superior distance is defined between the second plate and the first plate, and the second component is operable to be moved along the longitudinal axis relative to the first component to change the inferior-superior distance.

In some embodiments, the first component may include a housing and a support arm that extends posteriorly from a superior end of the housing to a posterior end. The support arm may have a first channel including a first lateral opening and the first plate removably coupled to its posterior end. The passageway may extend through the housing, and the arm of the second component may include a second channel including a second lateral opening that is aligned in an anterior-posterior direction with the first lateral opening of the first channel.

In some embodiments, the first plate may include a medial pad, a lateral pad spaced apart from the medial pad to define a slot sized to receive the posterior end of the support arm, a bracket connecting the medial pad to the lateral pad, and a moveable flange coupled to the bracket and configured to engage the posterior end of the support arm to secure the first plate to the first component.

In some embodiments, the first plate may have a first size and may be one plate of a plurality of first plates. Each first plate may have a size different from the first size and being configured to be selectively coupled to the support arm in place of the first plate.

In some embodiments, the posterior end of the arm of the second component may include a mounting peg that includes a bore that extends along the pivot axis. The second plate may include a body and an elongated pin extending anteriorly from the body along the pivot axis. The elongated pin may be received in the bore of the mounting peg such that the second plate is removably coupled to the arm of the second component. Additionally, in some embodiments, the posterior end of the support arm may include a groove that is sized to receive the mounting peg of the second component.

In some embodiments, the second plate may include a key extending from the body adjacent to the elongated pin. The mounting peg may include a keyway sized to receive the key to couple the second plate to the second component.

In some embodiments, the second plate may include a tab extending from the body, and the second component may include a flange that extends laterally from the posterior end of the arm. The flange may include a plurality of visual indicia to indicate a degree of tilt of the second plate relative to the first component based on an orientation of the tab relative to the flange.

In some embodiments, the second plate may have a first size and is one plate of a plurality of second plates. Each first plate may have a size different from the first size and may be configured to be selectively coupled to the arm of the second component in place of the first plate.

In some embodiments, the second component may include a plurality of teeth on the shaft. The first component may include a locking arm having a head configured to engage the plurality of teeth to lock the second component in a position along the longitudinal axis. The locking arm may be configured to pivot relative to the shaft to selectively engage the plurality of locking teeth.

In some embodiments, the orthopaedic surgical instrument may comprise a third component coupled to the first component and the second component. The third component may be operable to move the second component relative to the first component. The third component may include a handle that is positioned anterior of the first and second components. The handle may extend along a longitudinal axis extending transverse to the pivot axis.

Additionally, in some embodiments, the third component may include a first distractor arm extending posteriorly from the handle and a second distractor arm that is positioned superior of the first distractor arm. The first distractor arm may be attached to the superior end of the first component, and the second distractor arm may be attached to the superior end of the shaft of the second component and configured to move the second component. A piston may include an inferior end that is positioned in the handle and a superior end that is coupled to the second distractor arm. The piston may be moveable relative to the handle to move the second distractor arm relative to the first distractor arm to change the inferior-superior distance defined between the first plate and the second plate.

In some embodiments, the third component may include a lever coupled to the piston and the handle. The lever may be configured to pivot relative to the handle to move the piston relative to the handle from a first position at which the inferior-superior distance is a first distance to a second position at which the inferior-superior distance is a second distance greater than the first distance.

Additionally, in some embodiments, the third component may further include a body including the second distractor arm and a biasing element positioned between a distal surface of the body and a proximal surface of the piston. The biasing element may be operable to bias the piston a first distance from the second distractor arm.

In some embodiments, the piston may be moveable along an axis extending parallel to the longitudinal axis of the first component.

In some embodiments, the orthopaedic surgical instrument may further comprise a stylus coupled to the arm of the second component.

According to another aspect, a method of operating an orthopaedic instrument comprises selecting a tibial plate including a medial pad and a lateral pad configured to engage a proximal end of a patient's tibia, coupling the selected tibial plate to a superior end of a first instrument component, selecting a femoral plate including a medial pad and a lateral pad configured to engage a distal end of a patient's femur, coupling the selected femoral plate to a superior end of a second instrument component such that the selected femoral plate is operable to pivot relative to the second instrument component, coupling the second instrument component to the first instrument component such that an inferior-superior distance is defined between the selected femoral plate and the selected tibial plate, coupling a pair of distractor arms of a third instrument component to the first instrument component and the second instrument component, and moving a second distractor arm of the pair of distractor arms relative to a first distractor arm to move the selected femoral plate relative to the selected tibial plate and change the inferior-superior distance.

In some embodiments, selecting the tibial plate may include selecting a first tibial plate from a plurality of tibial plates. Each tibial plate of the plurality of tibial plates may have a different size.

In some embodiments, selecting the femoral plate may include selecting a first femoral plate from a plurality of tibial plates. Each femoral plate of the plurality of femoral plates may have a different size.

In some embodiments, coupling the selected tibial plate to the superior end of the first instrument component may include aligning a slot positioned between the medial pad and the lateral pad of the selected tibial plate with a posterior end of a support arm of the first instrument component, positioning the posterior end of the support arm in the slot of the selected tibial plate, and operating a movable flange to engage the posterior end of the support arm to secure the selected tibial plate to the first instrument component.

In some embodiments, coupling the selected femoral plate to the superior end of the second instrument component may include aligning an elongated pin of the selected femoral plate with a bore defined in the second instrument component. The elongated pin may be positioned anterior of the medial pad and the lateral pad of the selected femoral plate. Additionally, in some embodiments, coupling the selected femoral plate to the superior end of the second instrument component may include advancing the elongated pin into the bore.

In some embodiments, coupling the selected femoral plate to the superior end of the second instrument component may further include aligning a key of the selected femoral plate positioned adjacent to the elongated pin with a keyway defined in the second instrument component, advancing the key into a posterior opening of the keyway, and rotating the selected femoral plate to advance the key along a section of the keyway extending in a medial-lateral direction.

In some embodiments, the method may further comprise inserting the selected femoral plate and the selected tibial plate between a proximal end of a patient's tibia and a distal end of a patient's femur, and using a visual gauge of the third instrument component to determine a ligament tension while moving the first distractor arm of the pair of distractor arms relative to the second distractor arm and moving the selected femoral plate relative to the selected tibial plate.

In some embodiments, inserting the selected femoral plate and the selected tibial plate between the proximal end of the patient's tibia and the distal end of the patient's femur may include inserting the selected femoral plate and the selected tibial plate between an unresected proximal end of a patient's tibia and an unresected distal end of the patient's femur.

In some embodiments, inserting the selected femoral plate and the selected tibial plate between the proximal end of the patient's tibia and the distal end of the patient's femur may include inserting the selected femoral plate and the selected tibial plate between a resected proximal surface of the patient's tibia and a resected distal end of the patient's femur.

In some embodiments, the method may further comprise coupling a fourth instrument component to the second instrument component, and advancing a stylus of the fourth instrument component into engagement with an anterior surface of the patient's femur.

In some embodiments, the method may further comprise advancing a fixation pin through a bore defined in the fourth instrument into a distal surface of the patient's femur and removing the fourth instrument component from the second instrument component. The method may also comprise positioning a cutting block over the fixation pin into contact with the distal surface of the patient's femur.

In some embodiments, the method may comprise selecting a shim from a plurality of shims. Each shim may have a different thickness. The method may also comprise coupling the selected shim to the selected femoral plate.

Additionally, in some embodiments, moving the second distractor arm of the pair of distractor arms relative to the first distractor arm may include operating a lever of the third instrument component to move the second distractor arm.

In some embodiments, operating the lever of the third instrument component to move the second distractor arm may include rotating the lever to advance a piston coupled to the second distractor along a longitudinal axis extending in an inferior-superior direction.

According to another aspect, an orthopaedic surgical instrument system comprises a first orthopaedic surgical instrument including a tibial plate and a femoral plate configured to move relative to the tibial plate along an inferior-superior axis to change an inferior-superior distance and tilt relative to the tibial plate about a pivot axis extending traverse to the inferior-superior axis. The system also comprises a second orthopaedic surgical instrument including a pair of distractor arms that are configured to be coupled to the first orthopaedic surgical instrument. The second orthopaedic surgical instrument is operable to move a second distractor arm of the pair of distractor arms relative to a first distractor arm to move the femoral plate relative to the tibial plate along the inferior-superior axis.

In some embodiments, the second orthopaedic surgical instrument may include a handle extending along a longitudinal axis extending parallel to the inferior-superior axis, and a piston including an inferior end that is positioned in the handle and a superior end that is coupled to the second distractor arm. The piston may be moveable relative to the handle to move the second distractor arm relative to the first distractor arm.

In some embodiments, the second orthopaedic surgical instrument may further include a body including the second distractor arm, and a biasing element positioned between a distal surface of the body and a proximal surface of the piston. The biasing element may be operable to bias the piston a first distance from the second distractor arm.

In some embodiments, the system may further comprise a stylus configured to be coupled to the first orthopaedic surgical instrument.

According to another aspect, a method of performing a surgical procedure is disclosed. The method comprises coupling a tibial plate to a superior end of a lower balancer body, coupling a femoral plate to a superior end of an upper balancer body, inserting the femoral plate and the tibial plate into a gap defined between a proximal end of a patient's tibia and a distal end of a patient's femur, and moving the femoral plate away from the tibial plate to apply a load to the proximal end of a patient's tibia and the distal end of the patient's femur. The femoral plate is configured to tilt with the distal end of the patient's femur when the load is applied to the proximal end of the patient's tibia.

In some embodiments, moving the femoral plate away from the tibial plate may include operating a distraction instrument coupled to the upper balancer body and lower balancer body to move the femoral plate away from the tibial plate.

In some embodiments, the method may include determining an inferior-superior distance defined between the femoral plate and the tibial plate by measuring a distance moved by the upper balancer body relative to the lower balancer body.

In some embodiments, the method may include determining the load applied to the proximal end of a patient's tibia and the distal end of the patient's femur.

Additionally, in some embodiments, the method may include determining the tilt of the femoral plate by measuring a degree of tilt of the femoral plate relative to the lower balancer body.

In some embodiments, the method may include selecting a first size of at least one of a tibial plate including a medial pad and a lateral pad and a femoral plate including a medial pad and a lateral pad configured to engage a distal end of a patient's femur.

BRIEF DESCRIPTION OF THE DRAWINGS

The detailed description particularly refers to the following figures, in which.

DETAILED DESCRIPTION OF THE DRAWINGS

Figure 1:
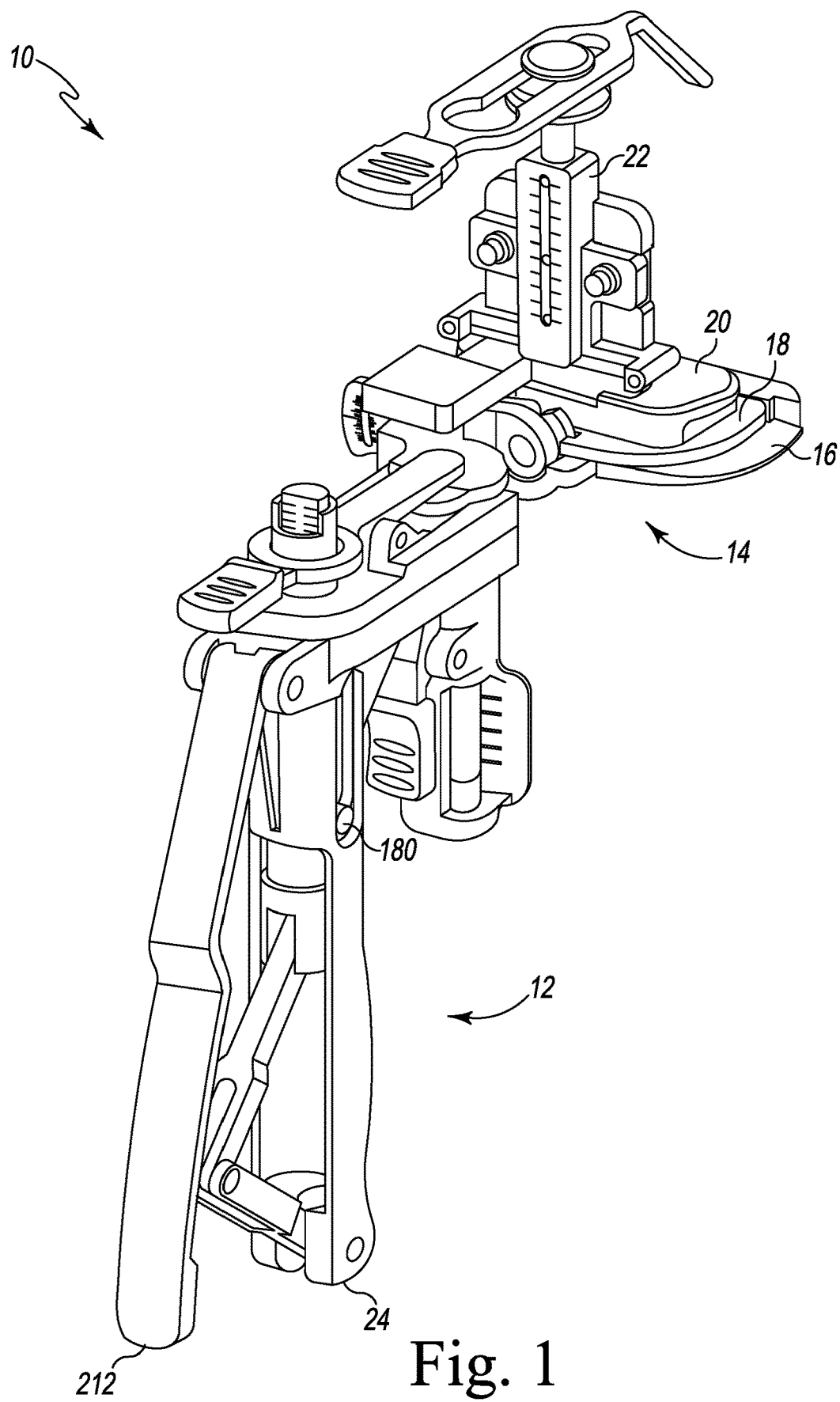
FIG. 1 is a perspective view of an orthopaedic instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic instrument system 10 for use during a knee arthroplasty surgical procedure is shown. The orthopaedic instrument system 10 includes a distraction instrument 12 that is selectively coupled to a balancer instrument assembly 14. The balancer instrument 14 includes a tibial paddle 16 and a femoral paddle 18 that is moveable relative the tibial paddle 16. As described in greater detail below, the distraction instrument 12 is configured to operate the balancer instrument 14 to selectively move the femoral paddle 18 relative to the tibial paddle 16 during a surgical procedure to assist the surgeon or other members of the surgical team in evaluating the patient's knee joint and selecting prosthetic components.

In the illustrative embodiment, the system 10 also includes a femoral shim 20 that is configured to be coupled to the femoral paddle 18. The balancer instrument 14 is also configured to be coupled to a femoral sizing instrument 22. The shim 20 and the femoral sizing instrument 22 are selectively coupled to the balancer instrument 14 to assist the surgeon or other user in sizing the prosthetic components (note that although both the shim 20 and the sizing instrument 22 are shown coupled to the balancer instrument 14 in FIG. 1 for clarity of description, in most embodiments, the two components would not be simultaneously secured to the balancer instrument 14 as will be become apparent below from the discussion relating to the surgical workflow). Moreover, although only a single shim 20 is shown, it should be appreciated that the system 10 may include a number of shims 20 of different sizes (e.g., thicknesses), which correspond to prosthetic components of different sizes and correspond to a flexion or extension gap assessable by a surgeon or other user between a patient's tibia and femur.

Figure 2:
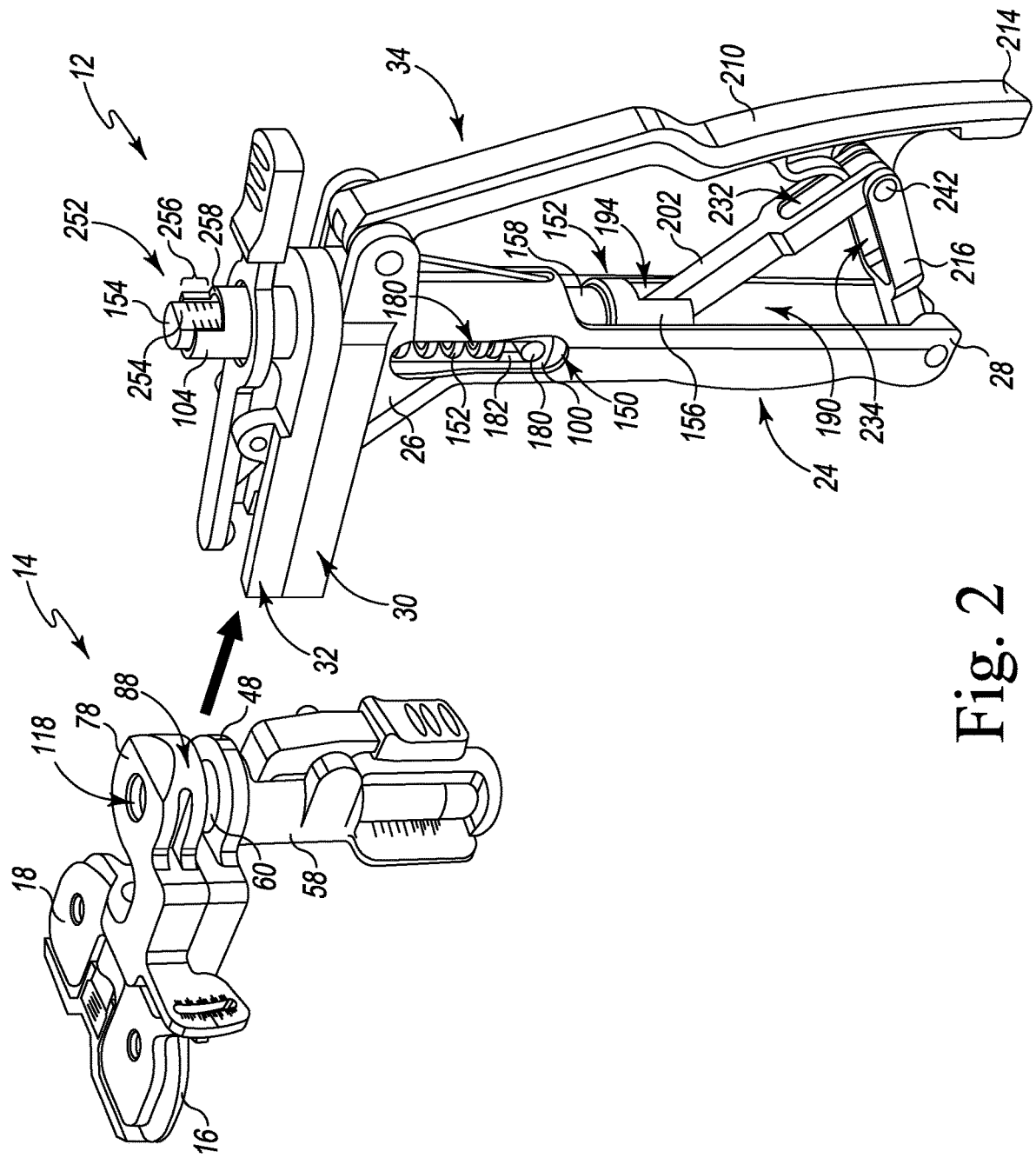
FIG. 2 is an exploded perspective view of a balancer instrument and a distraction instrument of the orthopaedic surgical instrument system of FIG. 1.

Referring now to FIG. 2, the distraction instrument 12 is shown disengaged from the balancer instrument 14. In the illustrative embodiment, the distraction instrument 12 includes an elongated handle 24 that extends from a proximal end 26 to a distal tip 28. The distraction instrument 12 also includes a stationary arm 30 that extends posteriorly from the proximal end 26 and a movable arm 32 that extends parallel to the stationary arm 30. The arms 30, 32 are configured to engage portions of the balancer instrument 14 to couple the instruments 12, 14 together. As described in greater detail below, a lever 34 of the distraction instrument 12 may be operated by a surgeon or other user to raise and lower the movable arm 32 relative to the stationary arm 30 and thereby selectively move the femoral paddle 18 of the balancer instrument 14 relative to the tibial paddle 16. It should be appreciated that in other embodiments both arms 30, 32 may be movable relative to the elongated handle 24 to move one or both of the paddles 16, 18 of the balancer instrument 14.

In the illustrative embodiment, the components of the distraction instrument 12 are formed from a metallic material such as, for example, stainless steel, unless noted otherwise. Each of the components are then assembled to form the distraction instrument 12. It should be appreciated that in other embodiments other materials may be used to form the components. For example, some of the components of the distraction instrument 12 may be formed from, or have a coating made of, a polymeric material such as, for example, polyethylene.

Figure 3:
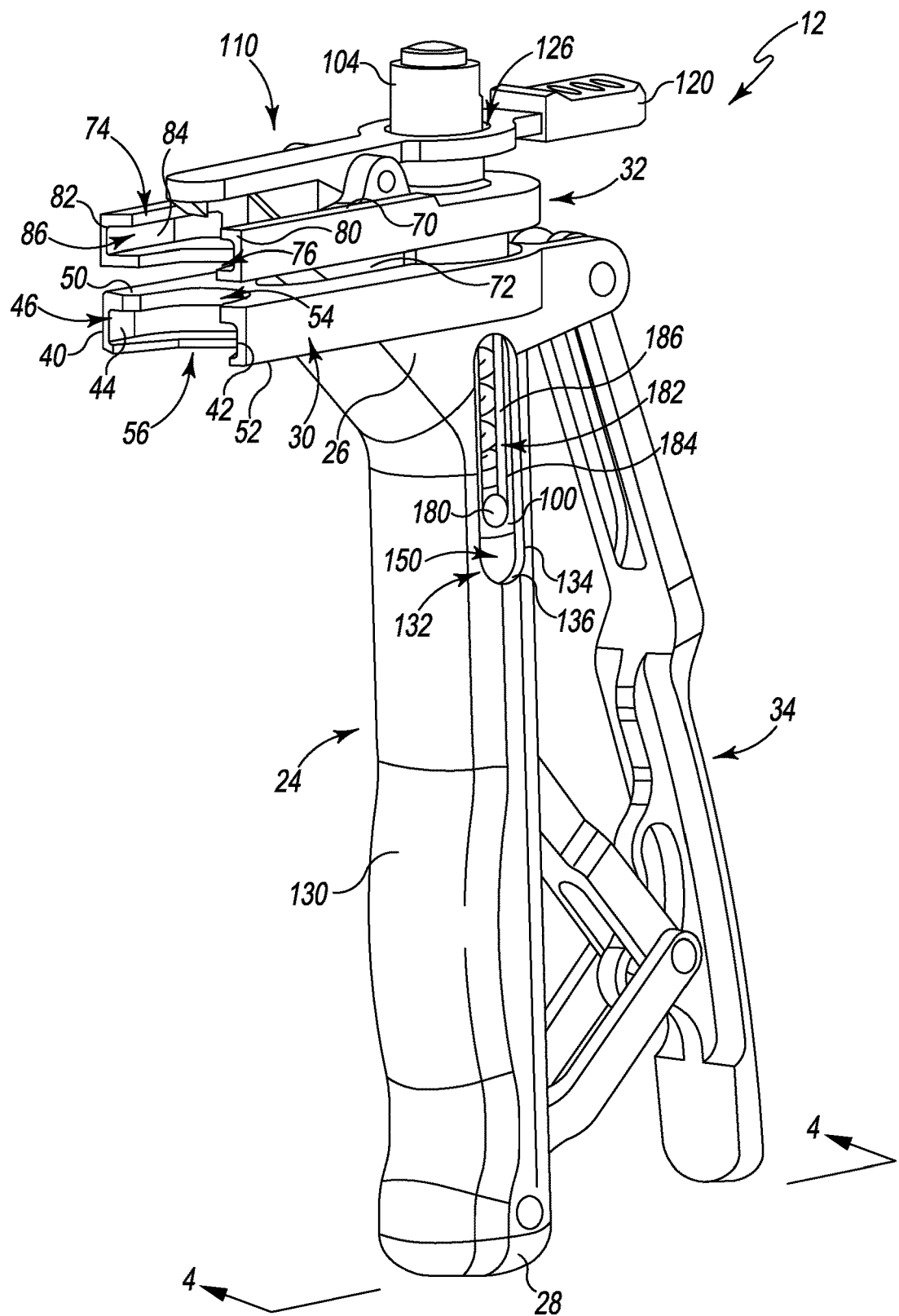
FIG. 3 is a perspective view of the distraction instrument of FIG. 2 showing an upper arm spaced apart from a lower arm of the distraction instrument.

Referring now to FIG. 3, the stationary arm 30 extends from the proximal end 26 of the handle 24 to a posterior tip 40. An opening 42 is defined in the posterior tip 40, and an inner wall 44 extends inwardly from the opening 42 to define a channel 46 in the stationary arm 30. The channel 46 is sized to receive a lower anterior flange 48 (see FIG. 2) of the balancer instrument 14.

The stationary arm 30 also includes a substantially planar upper surface 50 that is positioned opposite a lower surface 52. A pair of slots 54, 56 are defined in the surfaces 50, 52, respectively. Each slot 54, 56 opens into the channel 46 defined in the posterior tip 40. The slots 54, 56 are sized to receive a lower frame 58 and an elongated post 60, respectively, of the balancer instrument 14, as described in greater detail below.

The movable arm 32 includes an upper surface 70 that is positioned opposite a substantially planar lower surface 72. The lower surface 72 is shaped to engage the upper surface 50 of the stationary arm 30. Another pair of slots 74, 76 are defined in the surfaces 70, 72, respectively, and the slots 74, 76 are sized to receive an upper plate 78 and the elongated post 60, respectively, of the balancer instrument 14.

The movable arm 32 extends to a posterior tip 80 positioned above the posterior tip 40 of the stationary arm 30. An opening 82 is defined in the tip 80 of the arm 32, and an inner wall 84 extends inwardly from the opening 82 to define a channel 86, which is sized to receive an upper anterior flange 88 of the balancer instrument 14. Each of the slots 74, 76 opens into the channel 86 of the movable arm 32.

Figure 4:
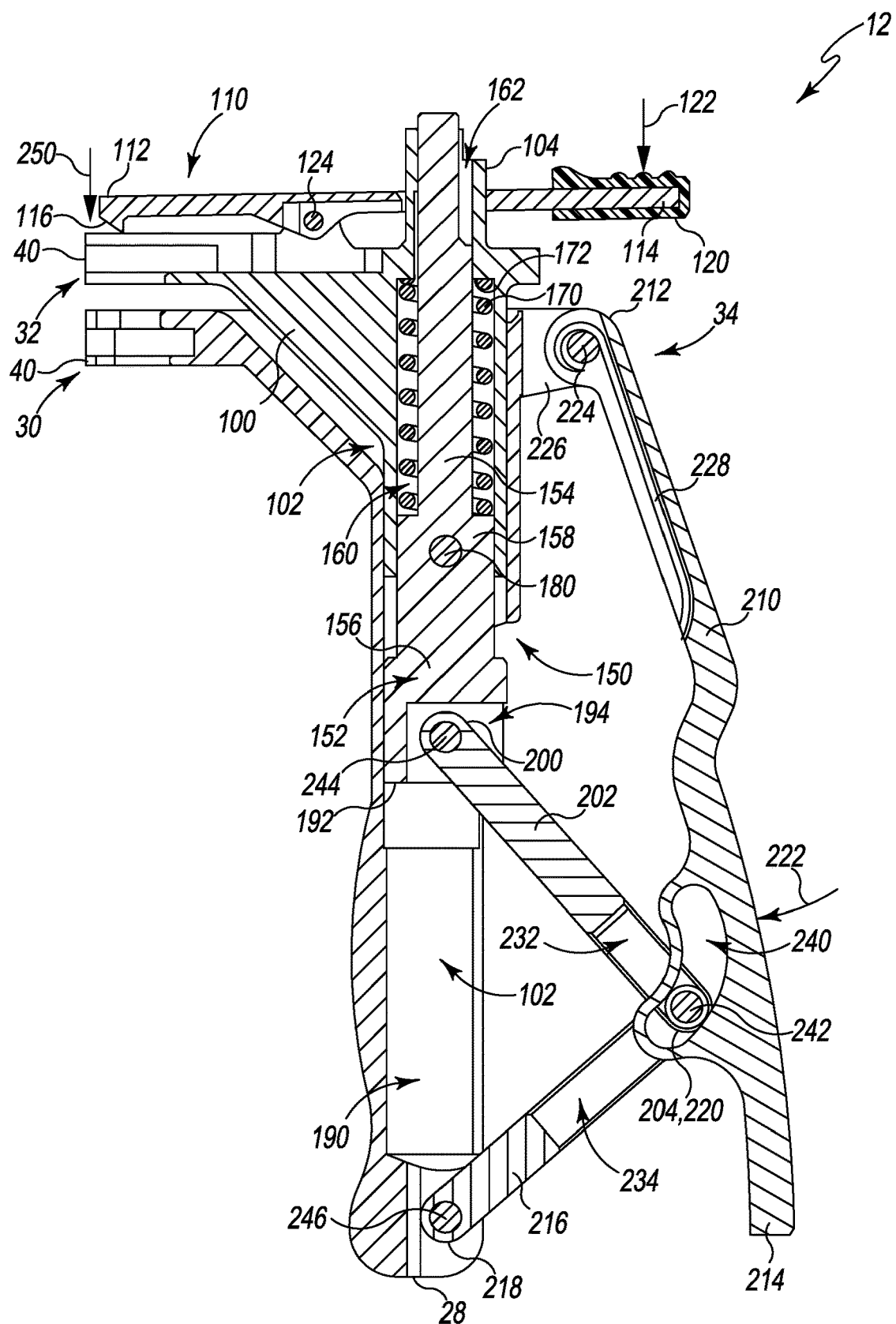
FIG. 4 is a cross-sectional view of the distraction instrument taken along the line 4-4 in FIG. 3.

As shown in FIG. 4, the movable arm 32 is attached to a wedge-shaped body 100 that extends distally into a bore 102 defined in the elongated handle 24. A post 104 extends proximally from the upper surface 70 of the movable arm 32 opposite the body 100. In the illustrative embodiment, the arm 32, the body 100, and the post 104 are formed as a single monolithic component. It should be appreciated that in other embodiments those components may be formed separately and later assembled using various techniques including, for example, brazing or welding.

The distraction instrument 12 also includes a retaining arm 110 that is pivotally coupled to the movable arm 32 via a pin 124. The retaining arm 110 extends from a posterior end 112 positioned adjacent the posterior tip 80 of the movable arm 32 to an anterior end 114 positioned above the lever 34 of the distraction instrument 12. A clip 116 extends distally from the posterior end 112 toward the upper slot 74 of the movable arm 32. The clip is sized to be received in a slot 118 defined in the balancer instrument 14 to secure the instruments 12, 14 to each other. A plastic grip 120 is formed over the anterior end 114. A biasing element such as a torsion spring (not shown) biases the retaining arm 110 in the position shown in FIGS. 2-4. The grip 120 is sized to receive a thumb or other finger of a surgeon or other user to permit the surgeon to press in the direction indicated by arrow 122. When sufficient force is applied, the bias exerted by the spring is overcome, and the retaining arm 110 is permitted to pivot into and out of engagement with the slot 118 of the balancer instrument 14.

Returning to FIG. 3, the post 104 of the distraction instrument 12 extends through a central opening 126 defined in the retaining arm 110. It should be appreciated that the opening 126 is sized to permit the retaining arm 110 to pivot and move relative to the post 104.

As described above, the elongated handle 24 extends from a proximal end 26 to a distal tip 28. In the illustrative embodiment, the handle 24 includes a contoured surface 130 that defines a handle grip. The elongated handle 24 also includes a medial oblong slot 132 and a lateral oblong slot (not shown) that are defined in the contoured surface 130. The configuration of the oblong slots is the same in the illustrative embodiment such that only the medial oblong slot 132 is described in detail. The slot 132 includes an opening 134, and an inner wall 136 extends inwardly from the opening 134 to the bore 102 defined in the handle 24. In that way, each of the oblong slots opens into the bore 102 in the illustrative embodiment.

The distraction instrument 12 includes an actuator 150 that is positioned in the bore 102 of the handle 24. The actuator 150 is configured to be operated by the lever 34 to raise and lower the movable arm 32 relative to the stationary arm 30. In the illustrative embodiment, the actuator 150 includes a piston 152 and an elongated shaft 154 that extends proximally from the piston 152 through the post 104. As shown in FIG. 4, the piston 152 includes a distal section 156 and a proximal section 158 that extends into a passageway 160 defined in the wedge-shaped body 100. The elongated shaft 154 of the actuator 150 extends from the proximal section 158 of the piston along the passageway 160 and through another passageway 162 extending through the arm 32 and the post 104. A biasing element, such as, for example, spring 170 is positioned in the passageway 160 between the distal section 156 of the piston 152 and an annular wall 172 positioned at the junction of the passageways 160, 162. As shown in FIG. 4, the distal section 156 of the piston 152 has a larger diameter than the proximal section 158, and the spring 170 is positioned around the proximal section 158.

In the illustrative embodiment, the piston 152 is movably coupled to the wedge-shaped body 100 via an elongated pin 180. As shown in FIGS. 2-3, the wedge-shaped body 100 includes a medial elongated slot 182 that is aligned with the medial oblong slot 132 of the elongated handle 24. The body 100 also includes a lateral elongated slot (not shown) having a configuration identical to the medial elongated slot 182. The slot 182 includes an opening 184, and an inner wall 186 extends inwardly from the opening 184 to the passageway 160 defined in the body 100. In that way, each of the elongated slots opens into the passageway 160 in the illustrative embodiment. The pin 180 extends outwardly from the piston 152 and is received in the medial elongated slot 182 and the lateral elongated slot, as shown in FIGS. 2-3. The bias exerted by the spring 170 biases the elongated pin 180 into contact with a distal section of the inner wall 186.

The distal section 156 of the piston 152 is sized such that the distal section 156 is prevented from entering the passageway 160 defined in the wedge-shaped body 100. As shown in FIG. 4, the distal piston section 156 is positioned in a channel section 190 of the bore 102, which includes a posterior-facing opening 192. A slot 194, which also has a posterior-facing opening, is defined in a distal end 196 of the distal piston 152. The slot 194 is sized to receive an end 200 of a link arm 202 of the lever 34, as described in greater detail below.

As described above, the lever 34 is configured to be operated by a surgeon or other user to raise and lower the movable arm 32 relative to the stationary arm 30. The lever 34 includes an actuation arm 210 that extends from a proximal end 212, which is pivotally coupled to the elongated handle 24, to a distal tip 214. The lever 34 also includes the link arm 202, which extends from the end 200 pivotally coupled to the piston 152 to an end 204 that is movably coupled to the actuation arm 210. Another link arm 216 extends from an end 218 pivotally coupled to the distal tip 28 of the elongated handle 24 to an opposite end 220 movably coupled to the actuation arm 210 and the link arm 202. In the illustrative embodiment, the movable arm 32 is moved away from the stationary arm 30 when a user applies a force to the actuation arm 210 in the direction indicated by arrow 222 in FIG. 4, as described in greater detail below.

The distraction instrument 12 includes an elongated pin 224 that extends through a clevis 226 attached to the elongated handle 24 and the proximal end 212 of the actuation arm 210 to couple the arm 210 to the elongated handle 24. The distraction instrument 12 also includes a biasing element, such as, for example, a spring 228 to bias the lever 34 with the distal tip 214 of the actuation arm 210 spaced apart from the distal tip 28 of the elongated handle 24, as shown in FIG. 1. The spring 228 is a torsion spring with an end wrapped around the elongated pin 224 and its opposite end positioned in a slot defined in the actuation arm 210.

The actuation arm 210 includes an anterior flange 230 that is positioned in a clevis 232 defined in the end 204 of the link arm 202 and another clevis 234 defined in the end 220 of the link arm 216. The anterior flange 238 includes a curved slot 240 that receives an elongated pin 242. The elongated pin 242 extends through the ends 204, 220 of the link arms 202, 216 to movably couple the link arms 202, 216 to the actuation arm 210. The opposite ends 200, 218 of the link arms 202, 216 are coupled to the piston 152 and elongated handle 24, respectively, via elongated pins 244, 246.

In use, a surgeon or other user may grasp the elongated handle 24 and the actuation arm 210 of the lever 34, wrapping their fingers around the anterior surface 130 of the elongated handle 24. If force is applied in the direction indicated by arrow 222 in FIG. 4, the engagement between the elongated pin 242, the anterior flange 238, and the link arm 202 causes the link arm 202 to exert a force on the piston 152 via the pin 244, thereby causing the piston 152 to advance upward along the bore 102. The spring constant of the spring 170 is sufficient to initially prevent compression of the spring 170 such that the piston 152 and the spring 170 cause the moveable arm 32 to move away from the stationary arm 30 to a raised position such as that shown in FIG. 4.

If a sufficient load or force is exerted on the posterior tip 40 of the moveable arm 32 in the direction indicated by arrow 250 in FIG. 4, the bias exerted by the spring 170 may be overcome and the spring 170 compressed, thereby permitting the elongated shaft 154 of the actuator 150 to move upward along the passageways 160, 162. The movement of the shaft 154 is guided by the interaction between the pin 180 extending through the piston 152 and the slot 184. As shown in FIG. 2, the distraction instrument 12 includes a gauge 252 that provides a visual indication of the amount of the load applied to the moveable arm 32.

In the illustrative embodiment, the gauge 252 includes a posterior surface 254 of the elongated shaft 154 of the actuator 150. A plurality of visual markings 256 are defined on the posterior surface 254, with each marking illustratively shown as a line corresponding to the load applied to the moveable arm 32. The gauge 252 also includes a reference surface 258 included on the post 104 that may be used to identify which marking 256 is associated with the applied load. It should be appreciated that in other embodiments the gauge may take the form of other measurement devices such as, for example, an electronic load sensor or other mechanism.

Figure 5:
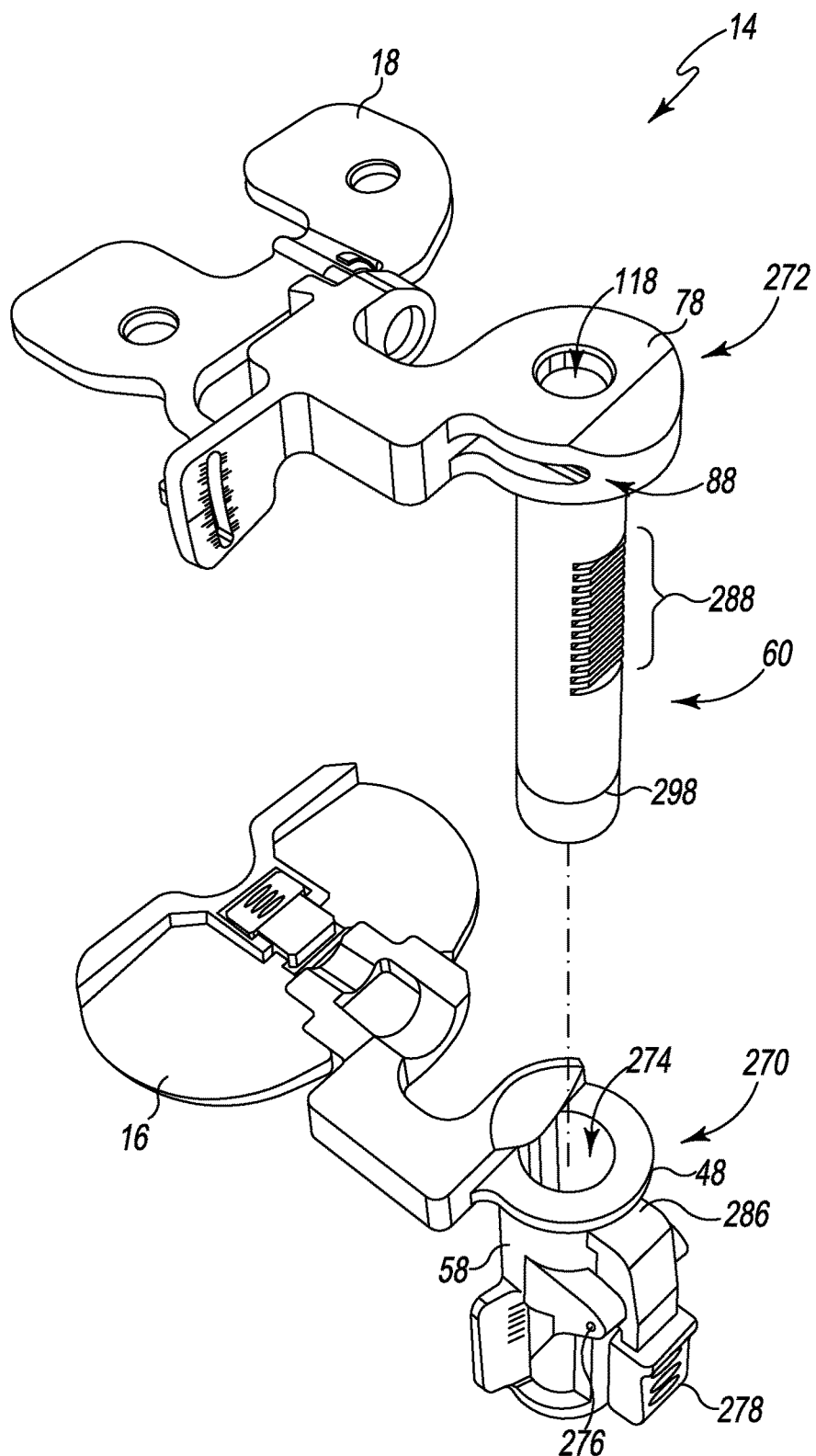
FIG. 5 is an exploded perspective view of the balancer instrument of FIG. 2.

As described above, the moveable arm 32 and the stationary arm 30 of the distraction instrument 12 are configured to engage the balancer instrument 14 such that movement of the moveable arm 32 causes the femoral paddle 18 of the balancer instrument 14 to move relative to the tibial paddle 16. Referring now to FIG. 5, the balancer instrument 14 includes a lower body 270 that is configured to be selectively coupled to a tibial paddle 16, an upper body 272 that is configured to be selectively coupled to a femoral paddle 18, and an elongated post 60 extending from the upper balancer body 272 to be received in a passageway 274 defined in the lower balancer body 270. Although only a single tibia paddle 16 and a single femoral paddle 18 are shown, it should be appreciated that the system 10 may include a number of paddle 16, 18 of different sizes (e.g., medial-lateral widths), which correspond to prosthetic components of different sizes.

In the illustrative embodiment, the components of the balancer instrument 14, including the paddles 16, 18, are formed from a metallic material such as, for example, stainless steel, unless noted otherwise. Each of the components are then assembled to form the balancer instrument 14. It should be appreciated that in other embodiments other materials may be used to form the components. For example, some of the components of the distraction and strength may be formed from a polymeric material just, for example, polyethylene.

Figure 6:
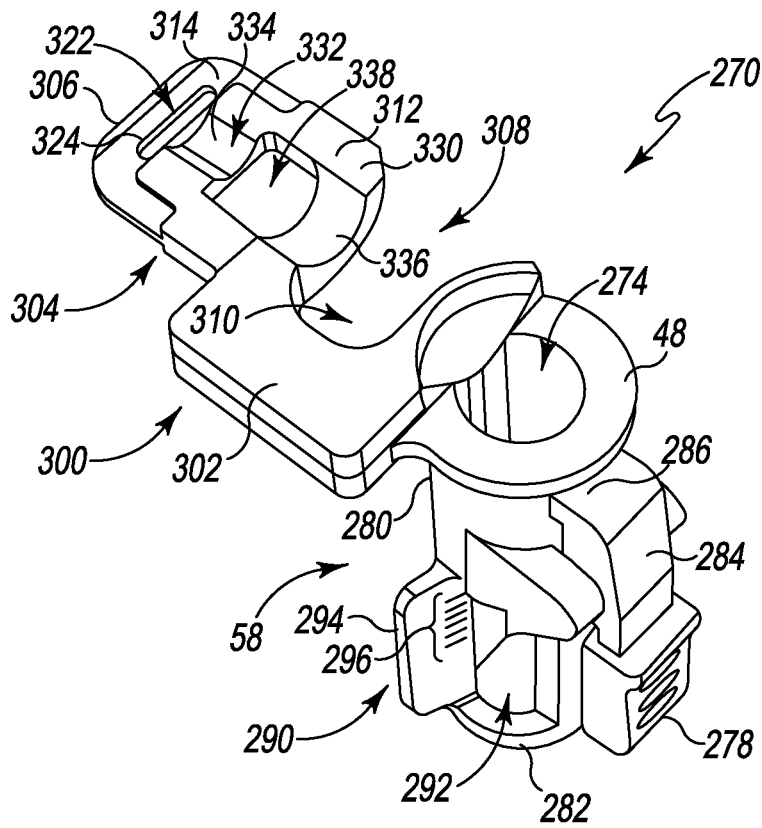
FIG. 6 is a perspective view of a housing of the balancer instrument of FIG. 5.

As shown in FIG. 6, the lower balancer body 270 includes a lower frame 58 that extends from a proximal end 280 to a distal end 282. A lower anterior flange 48 of the balancer instrument 14 is attached to the proximal end 280 of the frame. As described above, the anterior flange 48 is sized to be received in the channel 46 of the stationary arm 30 of the distraction instrument 12.

The passageway 274 extends from an opening defined in the proximal end 280 of the lower frame 58 to another opening defined in the distal end 282. The lower balancer body 270 also includes a lever 284 that is pivotally coupled to the lower frame 58. As described in greater detail below, the lever 284 includes a tab 286 sized to engage a plurality of teeth 288 defined on the elongated post 60 of the upper balancer body 272 to lock the upper balancer body 272 (and hence the femoral paddle 18) in position relative to the tibial paddle 16. The lower balancer body 270 also includes an elongated pin 276 that extends through the lever 284 and the lower frame 58 to attach the lever to the frame 58. As shown in FIG. 6, the lever 284 also includes a grip 278 that is shaped to permit a surgeon or other user to operate the lever 284 to move the tab 286 into and out of engagement with the teeth 288. The lower balancer body 270 includes a spring (not shown) to bias the lever 284 in a locking position in which the tab 286 is positioned to engage the teeth 288.

A gauge 290 is attached to the lower frame 58 to provide a visual indication of the distance moved by the femoral paddle 18 relative to the tibial paddle 16. In the illustrative embodiment, the gauge 290 includes a longitudinal slot 292 positioned on each side of lever 284, which open into the passageway 274. The slots 292 are sized such that the elongated post 60 is visible to a surgeon or other user when positioned in the passageway 274. The gauge 290 also includes a pair of plates 294 extending from the lower frame 58 adjacent to the slots 292. A plurality of visual markings 296 are defined on each plate 294, with each marking corresponding to a distance moved by femoral paddle 18 relative to the tibial paddle 16. The distance is indicated by another visual marking, such as, for example, line 298 (see FIG. 5) on the elongated post 60, which may be aligned with any of the markings 296. It should be appreciated that in other embodiments the gauge may take the form of other measurement devices such as, for example, an electronic distance sensor or other mechanism.

The lower balancer body 270 includes a support arm 300 that extends posteriorly from the proximal end 280 of the lower frame 58. The support arm 300 includes an anterior section 302 connected to the proximal end 280 and a posterior section 304 that is connected to the anterior section 302. The posterior section 304 extends to a posterior tip 306. As shown in FIG. 6, the anterior section 302 has a lateral opening 308 and a channel 310 that extends medially from the lateral opening 308. The opening 308 and the channel 310 are sized to receive a portion of the patient's ligaments during a surgical procedure to permit the balancer instrument 14 to be positioned in patient's knee joint without disrupting the ligaments.

The posterior section 304 of the support arm 300 includes a main plate 312 attached to the anterior arm section 302 and a mounting flange 314 that extends from the main plate 312 to the posterior tip 306. In the illustrative embodiment, the flange 314 has a smaller thickness than the main plate 312 and is sized to be positioned in a channel 320 defined in each tibial plate 318. The flange 314 has a planar upper surface that is positioned opposite a planar lower surface in the illustrative embodiment.

The posterior arm section 304 also includes an oblong slot 322 that extends through the upper and lower surfaces of the mounting flange 314. As shown in FIG. 6, the oblong slot 322 is defined by an inner wall 324. The slot 322 and wall 324 are sized and shape to receive and engage a tab 326 of the tibial plate 318 to selectively secure each tibial plate 318 to the support arm 300 of the lower balancer body 270. In that way, the oblong slot 322, the inner wall 324, and the tab 326 form part of a fastening mechanism to selectively couple each tibial plate 318 to the lower balancer body 270. It should be appreciated that in other embodiments the balancer instrument 14 may include other fastening devices such, for example, screws, pins, levers, and so forth to couple the lower balancer body 270 to each tibial plate 318.

The main plate 312 has an upper surface 330 that is offset from the flange 314 of the support arm 300. A longitudinal groove 332 is defined in the upper surface 330. As shown in FIG. 6, the groove 332 is partially defined by a pair of concave curved surfaces 334, 336, which are separated by an opening 338 that extends through the main plate 312.

Figure 7:
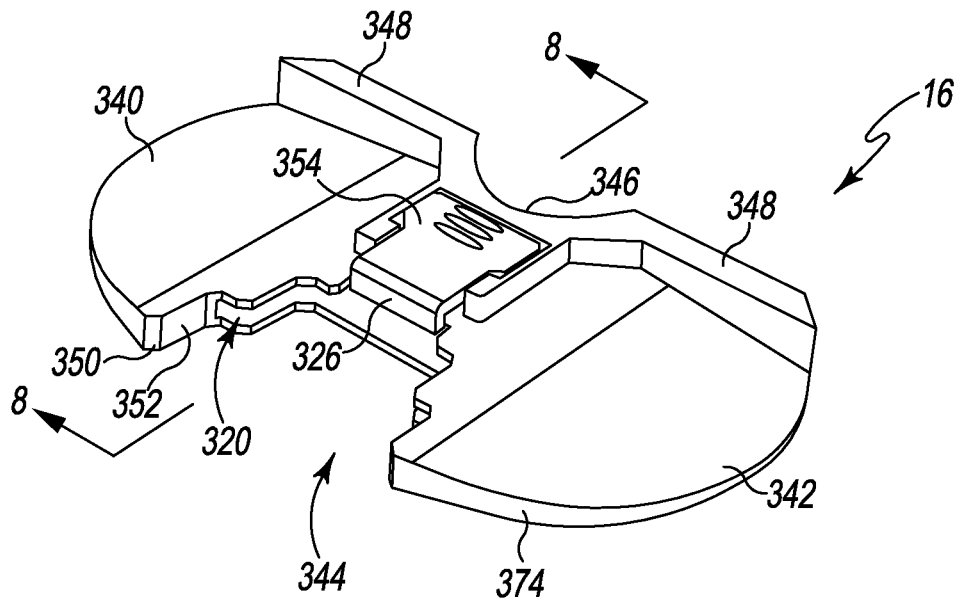
FIG. 7 is a perspective view of a tibial paddle of the balancer instrument of FIG. 5.

Referring now to FIG. 7, each tibial paddle or plate 16 of the system 10 includes a medial pad 340 and a lateral pad 342 that is spaced apart from the medial pad 340. The pads 340, 342 cooperate to define an anterior slot 344 that is sized to receive the posterior section 304 of the support arm 300. The tibial paddle 16 also includes a bracket 346 that connects the medial pad 340 to the lateral pad 342. In the illustrative embodiment, the tibial paddle 16 also includes a posterior wall 348 that extends upwardly from the pads 340, 342.

Figure 8:
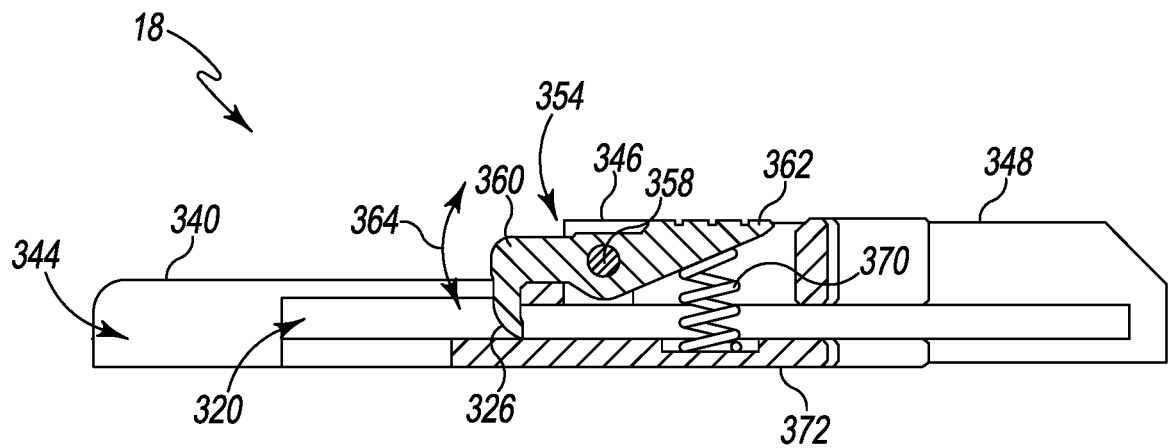
FIG. 8 is a cross-sectional elevation view of the tibial paddle taken along the line 8-8 in FIG. 7.

The tibial paddle 16 includes an anterior opening 350 that is defined between the pads 340, 342 and a sidewall 352 that extends posteriorly from the opening 350 to the bracket 346 to define the anterior slot 344. As shown in FIG. 7, the sidewall 352 is stepped inwardly and is shaped to match the outer geometries of the main plate 312 of the support arm 300 of the lower balancer body 270 and the flange 314. As described above, the tibial paddle 16 also includes a channel 310 sized to receive the flange 314, which is defined in the sidewall 352 on each side of the anterior slot 344 and extends into the bracket 346, as shown in FIGS. 7-8.

As described above, the tibial paddle 16 also includes a tab 326 that is sized to be positioned in the oblong slot 322 of the flange 314 to couple the lower balancer body 270 to the tibial paddle 16. In the illustrative embodiment, the tab 326 is included on a moveable flange 354 that is pivotally coupled to the bracket 346. As shown in FIG. 8, the flange 354 includes a lever 356 that is attached to the bracket 346 via an elongated pin 358 extending through the lever 356 and the bracket 346. The tab 326 extends outwardly from one end 360 of the lever 356, and the opposite end 362 includes a knurled surface sized to permit a surgeon or other user to operate the lever 356 to pivot it relative to the bracket 346. As indicated by arrows 364 in FIG. 8, the lever 356 may be operated to move between the lowered position shown in FIG. 8 in which the tab 326 is positioned to be received in the oblong slot 322 of the support arm 300 and a raised position in which a gap is formed between the tab 326 and the bracket 346. When in the raised position, the gap is sized to permit the support arm 300 to be advanced into or removed from the channel 320. The tibial paddle 16 also includes a biasing element such as, for example, spring 370 that is positioned between the bracket 346 and the end 362 of the lever 356. The spring 370 is sized to exert a bias on the lever 356 to maintain the lever 356 in the lowered position shown in FIG. 8.

In the illustrative embodiment, the tibial paddle 16 includes a substantially planer bottom surface 372 and an outer wall 374 that is shaped to match the outer geometry of the proximal end of a patient's tibia. As described in greater detail below, the planar bottom surface 372 is configured to be positioned on a resected surface 376 (see FIG. 16) of the patient's tibia. It should be appreciated that in other embodiments the tibial paddle 16 may include a contoured bottom surface shaped to engage the proximal end of a patient's tibia prior to resection.

Figure 9:
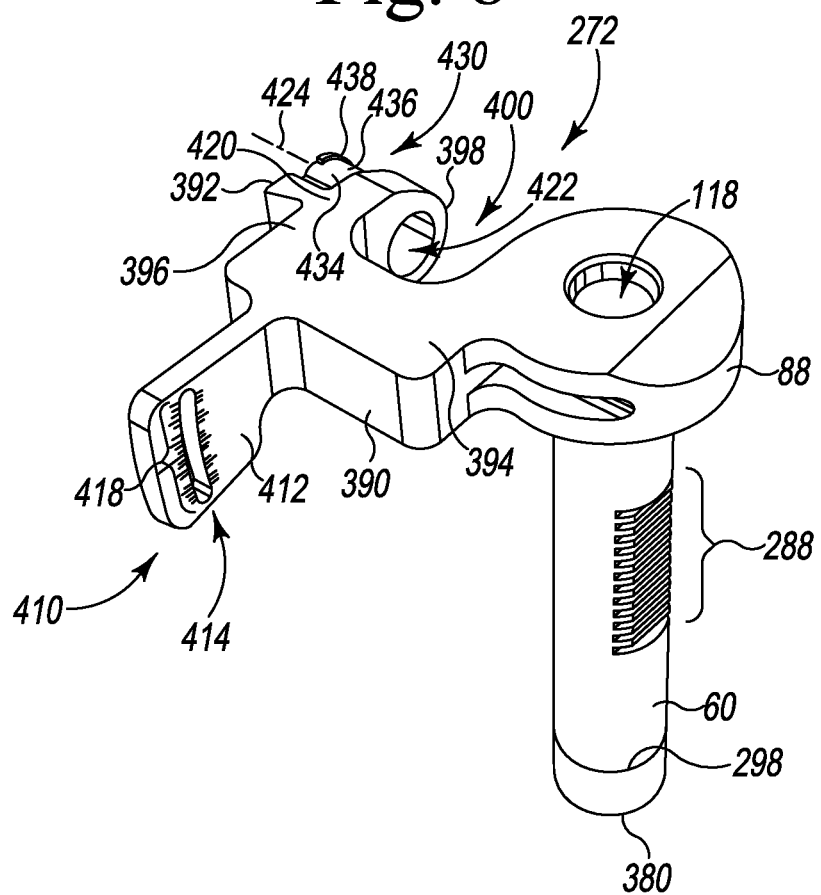
FIG. 9 is a perspective view of a post and a support arm of the balancer instrument of FIG. 5.

Referring now to FIG. 9, the elongated post 60 extends from the upper balancer body 272 to a distal tip 380. In the illustrative embodiment, the post 60 includes a cylindrical outer surface 382. It should be appreciated that in other embodiments the post 60 may take other geometric shapes to match the shape of the passageway 274 defined in the lower balancer body 270. The plurality of teeth 288 of the post 60 are defined on the anterior side of the outer surface 382. As described above, the teeth 288 are sized and shaped to engage the tab 286 of the lever 284 to lock the upper balancer body 272 (and hence the femoral paddle 18) in position relative to the lower balancer body 270 (and hence the tibial paddle 16). It should be appreciated that the teeth 288 may be separated from one another in relatively small increments, such as 1 mm, to allow for precise measurement of the femoral/tibial gap.

The upper balancer body 272 includes the upper anterior flange 88 of the balancer instrument 14. As described above, the flange 88 is sized and shaped to be received in a channel 86 to couple the upper balancer body 272 (and hence the femoral paddle 18) to the moveable arm 32 of the distraction instrument 12. A support arm 390 extends posteriorly from the flange 88 to a posterior tip 392 configured to engage the femoral paddle 18. The support arm 390 includes an anterior section 394 connected to the flange 88 and a posterior section 396 that is connected to the anterior section 394. The posterior section 396 extends to the posterior tip 392. As shown in FIG. 9, the anterior section 394 has a lateral opening 398 and a channel 400 that extends medially from the lateral opening 398. The opening 398 and the channel 400 are sized to receive a portion of the patient's ligaments during a surgical procedure to permit the balancer instrument 14 to be positioned in patient's knee joint without disrupting the ligaments. In the illustrative embodiment, the opening 398 and the channel 400 are aligned with the opening 308 and channel 310 of the lower balancer body 270 to define a single channel 474 (see FIG. 12) in the balancer instrument 14.

A gauge 410 is attached to the upper balancer body 272 to provide a visual indication of the angle the femoral paddle 18 relative to the tibial paddle 16. In the illustrative embodiment, the gauge 410 includes a flange or plate 412 extending medially from the anterior section 394 of the support arm 390 and a curved slot 414 that extends through the plate 412. The slot 414 is sized such that a tab 416 (see FIG. 10) of the femoral paddle 18 is visible to a surgeon or other user through the slot 414 when the femoral paddle 18 is coupled to the upper balancer body 272. The gauge 410 also includes a plurality of visual markings 418 defined on the plate 412, with each marking corresponding to an angle of the femoral paddle 18 relative to the tibial paddle 16. It should be appreciated that in other embodiments the gauge may take the form of other measurement devices such as, for example, an electronic angle sensor or other mechanism.

The posterior section 396 of the support arm 390 of the upper balancer body 272 includes a mounting peg 420 at the posterior tip 392. A longitudinal bore 422 extends from the posterior side of the peg 420 and opens into the channel 400. The bore 422 extends along a pivot axis 424 about which the femoral paddle 18 may pivot relative to the upper balancer body 272, as described in greater detail below. The mounting peg 420 includes a convex outer surface 426 that is shaped and sized to be received in the groove 332 defined in the lower balancer body 270.

As shown in FIG. 9, a keyway 430 is defined in the convex outer surface 426 of the mounting peg 420. The keyway 430 is sized to receive a key 432 (see FIG. 10) of the femoral paddle 18 to couple the paddle to the mounting peg 420, as described in greater detail below. The keyway 430 in the illustrative embodiment is defined by an inner wall 438 and includes a track 434 that extends in an anterior-posterior direction and another track 436 that extends in a lateral direction from the track 434. The track 436 extends around a portion of the outer circumference of the mounting peg 420 such that the keyway illustratively has two orthogonal sections. It should be appreciated that in other embodiments other combinations of keys, slots, and fasteners may be used to couple the femoral paddle 18 to the upper balancer body 272.

Figure 10:
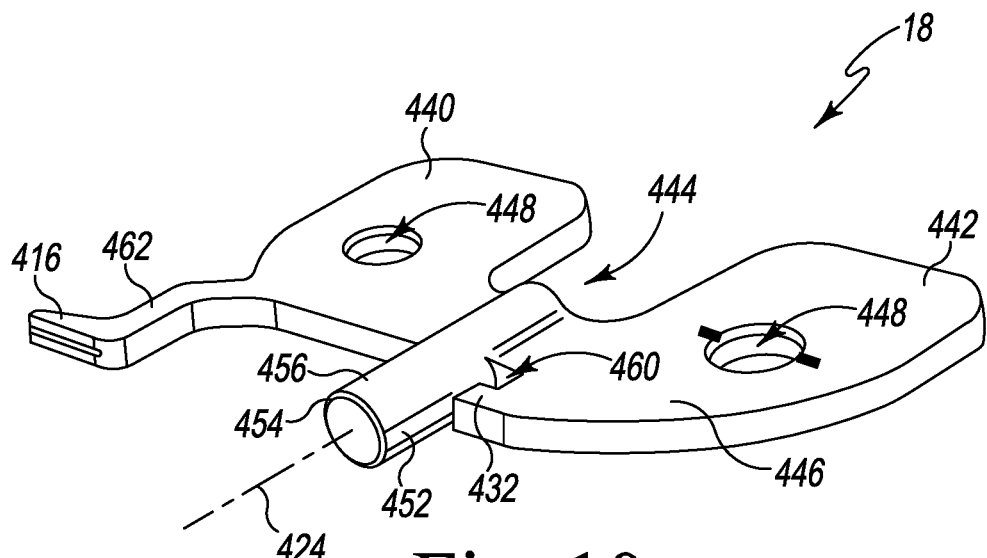
FIG. 10 is a perspective view of a femoral paddle of the balancer instrument of FIG. 5.

Referring now to FIG. 10, each femoral paddle or plate 18 includes a medial pad 440, a lateral pad 442 that is spaced apart from the medial pad 440, and a bracket 444 that connects the pads 440, 442. Each of the pads 440, 442 includes a proximal surface 446 configured to engage a resected surface of a distal end of a patient's femur or engage one of the femoral shims 20. Each of the pads 440, 442 also includes an opening 448 that extends through the pads 440, 442 and is sized to receive the posts 450 of each shim 20.

The bracket 444 of the femoral paddle 18 includes an elongated shaft 452 that extends outwardly to an anterior end 454. The elongated shaft 452 is sized and shaped to be received in the bore 422 defined in the mounting peg 420 of the upper balancer body 272. The shaft 452 includes a cylindrical outer surface 456 to permit the femoral paddle 18 to pivot relative to the upper balancer body 272.

As described above, each femoral paddle 18 includes a key 432 that is sized to be received in the keyway 430 of the upper balancer body 272. In the illustrative embodiment, the key 432 extends from the lateral pad 442 toward the elongated shaft 452. A slot 460 is defined between the key 432 and the elongated shaft 452, which is sized to receive the walls lining the keyway 430 of the upper balancer body 272.

Each femoral paddle 18 also includes the tab 416 of the gauge 410. As shown in FIG. 10, the tab 416 is positioned at the end of an arm 462 extending from the medial pad 440. As described above, the tab 416 is positioned to be aligned with the curved slot 414 of the upper balancer body 272 when the femoral paddle 18 is coupled to the body 272.

Figure 11:
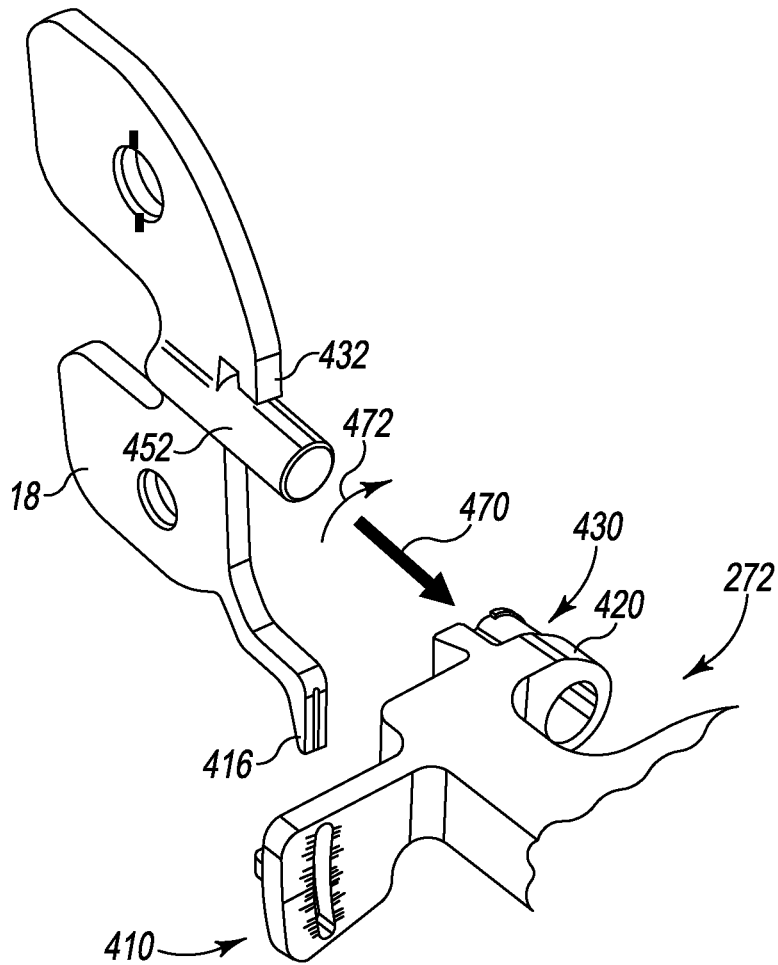
FIG. 11 is an exploded perspective view of the balancer instrument of FIG. 5 showing the femoral paddle aligned with the support arm.

To assemble a femoral paddle 18 to the upper balancer body 272, a surgeon or other user may align the elongated shaft 452 of the paddle with the longitudinal bore 422 defined in the mounting peg 420 of the balancer body, as shown in FIG. 11. The user may rotate the paddle 18 relative to the body 272 to align the key 432 with the posterior opening of the keyway 430 (i.e., the posterior end of the track 434). The user may then advance the shaft 452 in the direction indicated by arrow 470 to position the shaft 452 in the bore 422 and the key 432 of the paddle 18 in the track 434 of the keyway 430. With the key 432 aligned with the lateral track 436 of the keyway 430, the user may rotate the paddle 18 in the direction indicated by arrow 472 to advance the key 432 along the track 436, thereby securing the paddle 18 to the upper balancer body 272.

Figure 12:
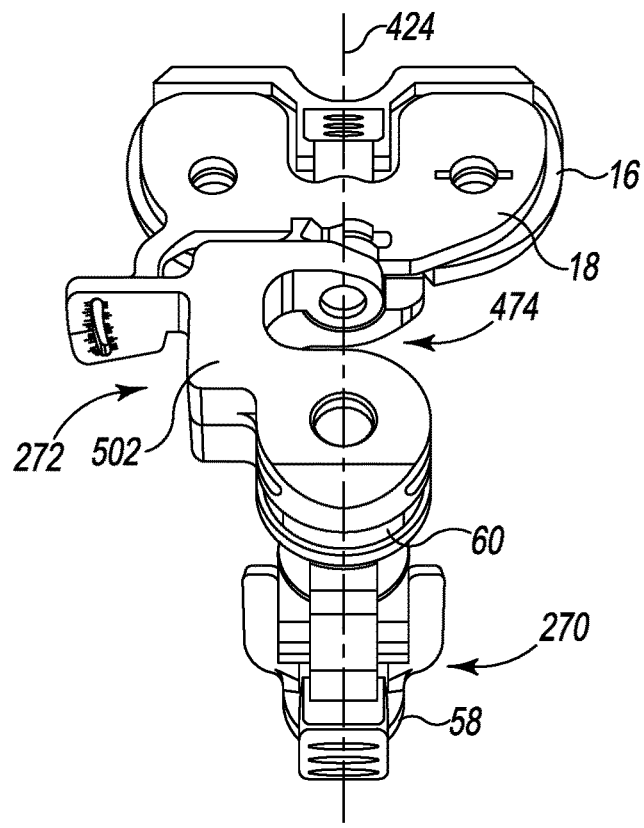
FIG. 12 is a perspective view of the balancer instrument of FIG. 5.
Figure 13:
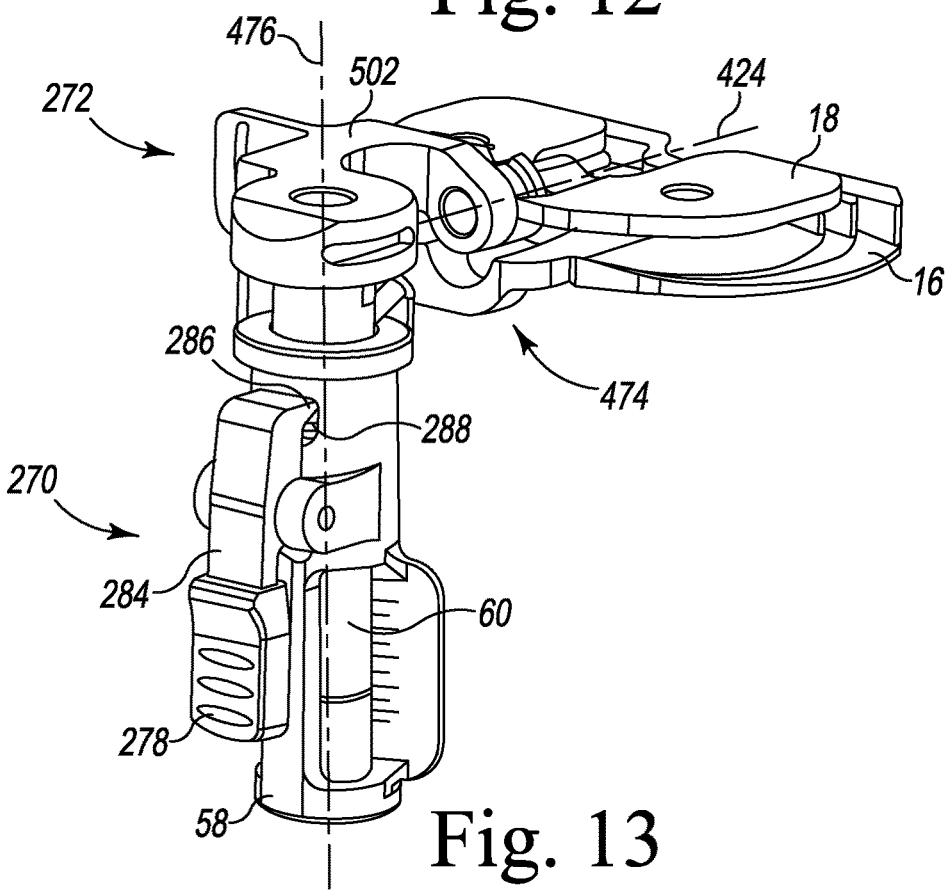
FIG. 13 is another perspective view of the balancer instrument of FIG. 5 showing the femoral paddle spaced apart from the tibial paddle.

Referring now to FIGS. 12-13, the upper balancer body 272 may be assembled with the lower balancer body 270 by inserting the post 60 into the passageway 274 defined in the lower balancer body 270. As described above, the opening 398 and the channel 400 of the upper body 272 are aligned with the opening 308 and channel 310 of the lower body 270 to define a single channel 474 in the balancer instrument 14. Additionally, the pivot axis 424 of the femoral paddle 18 extends through the channel 274 and is aligned with the longitudinal axis 476 of the elongated post 60 (and lower frame 58). A user may remove the elongated post 60 from the passageway 274 by operating the lever 284 to disengage the tab 286 from the teeth 288 of the elongated post 60.

Figure 14:
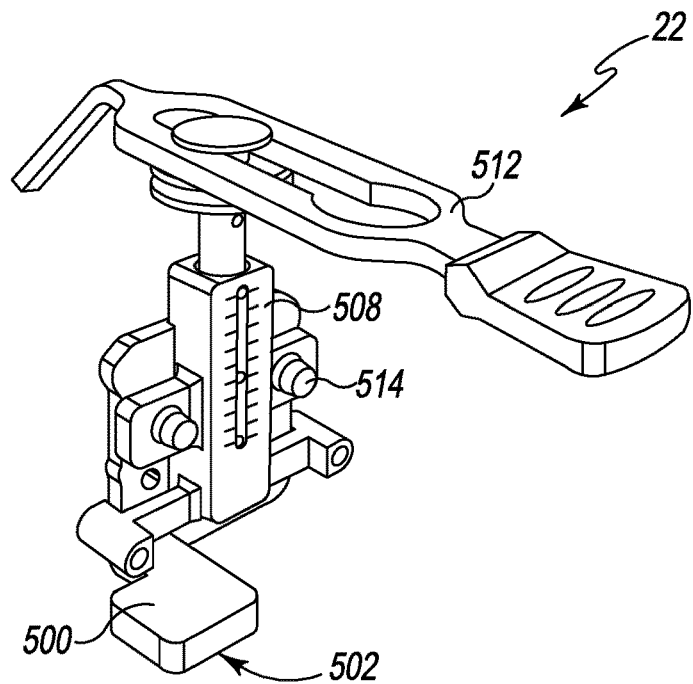
FIG. 14 is a perspective view of a femoral sizing instrument of the orthopaedic instrument system of FIG. 1.
Figure 15:
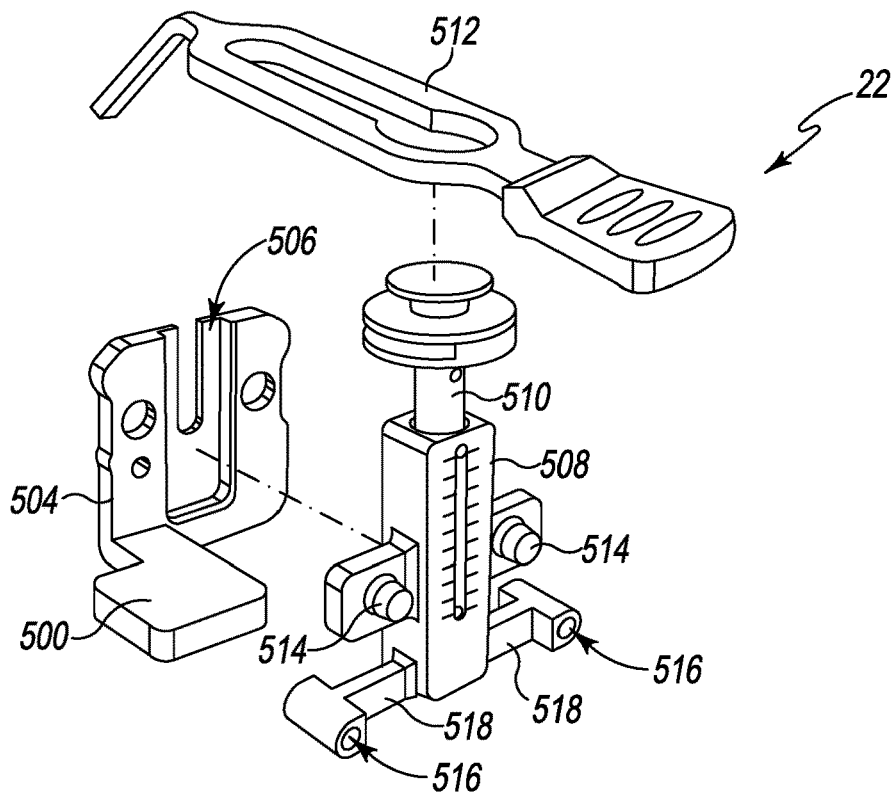
FIG. 15 is an exploded perspective view of the femoral sizing instrument of FIG. 14.

As described above, the system 10 also includes a femoral sizing instrument 22 that is configured to be coupled to the balancer instrument 14. Referring now to FIGS. 14-15, the sizing instrument 22 includes a base 500 that is configured to be positioned on the anterior section 394 of the support arm 390 of the balancer instrument 14. In the illustrative embodiment, the base 500 and the anterior arm section 394 having matching planar surfaces 502, which are engaged when the sizing instrument 22 is coupled to the balancer instrument 14. The base 500 is illustratively includes a magnetic material that interacts with the metallic material of the support arm 390 to secure the instruments together. It should be appreciated that in other embodiments the instruments may include any combination of screws, pegs, or other fasteners to attach the sizing instrument 22 to the instrument 14.

The sizing instrument 22 is modular and may be dissembled during surgeries for cleaning and/or repair. A posterior plate 504 extends upwardly from the base 500 and includes a longitudinal channel 506. The sizing instrument 22 also includes an elongated body 508 that is sized to be positioned in the longitudinal channel 506, a shaft 510 that extends into the elongated body 508, and a stylus 512 that is pivotally coupled to the shaft 510. In the illustrative embodiment, the shaft 510 is moveable relative to the elongated body 508 to lower and raise the stylus 512. The sizing instrument 22 includes a pair of retained screws 514 that are configured to secure the body 508 to the plate 504. A pair of fixation pin guides 516 are defined in arms 518 attached to the elongated body 508. Each guide 516 is sized to receive a fixation pin 520 (see FIG. 22) configured to be secured to a patient's bone.

Referring now to FIGS. 16-22, some steps of a surgical procedure utilizing the system 10 are shown. To use the system 10 during a procedure, a surgeon or other user may assemble the components of the balancer instrument 14 together and select a tibial paddle 16 and a femoral paddle 18 for use with a particular patient. As described above, the paddles 16, 18 may be provided in different sizes, which correspond to different sizes of implants. It should also be appreciated that the balancer instrument may be provided in a left or right knee configuration. In each configuration, the channel 474 defined by the upper and lower balancer bodies faces or opens laterally.

Figure 16:
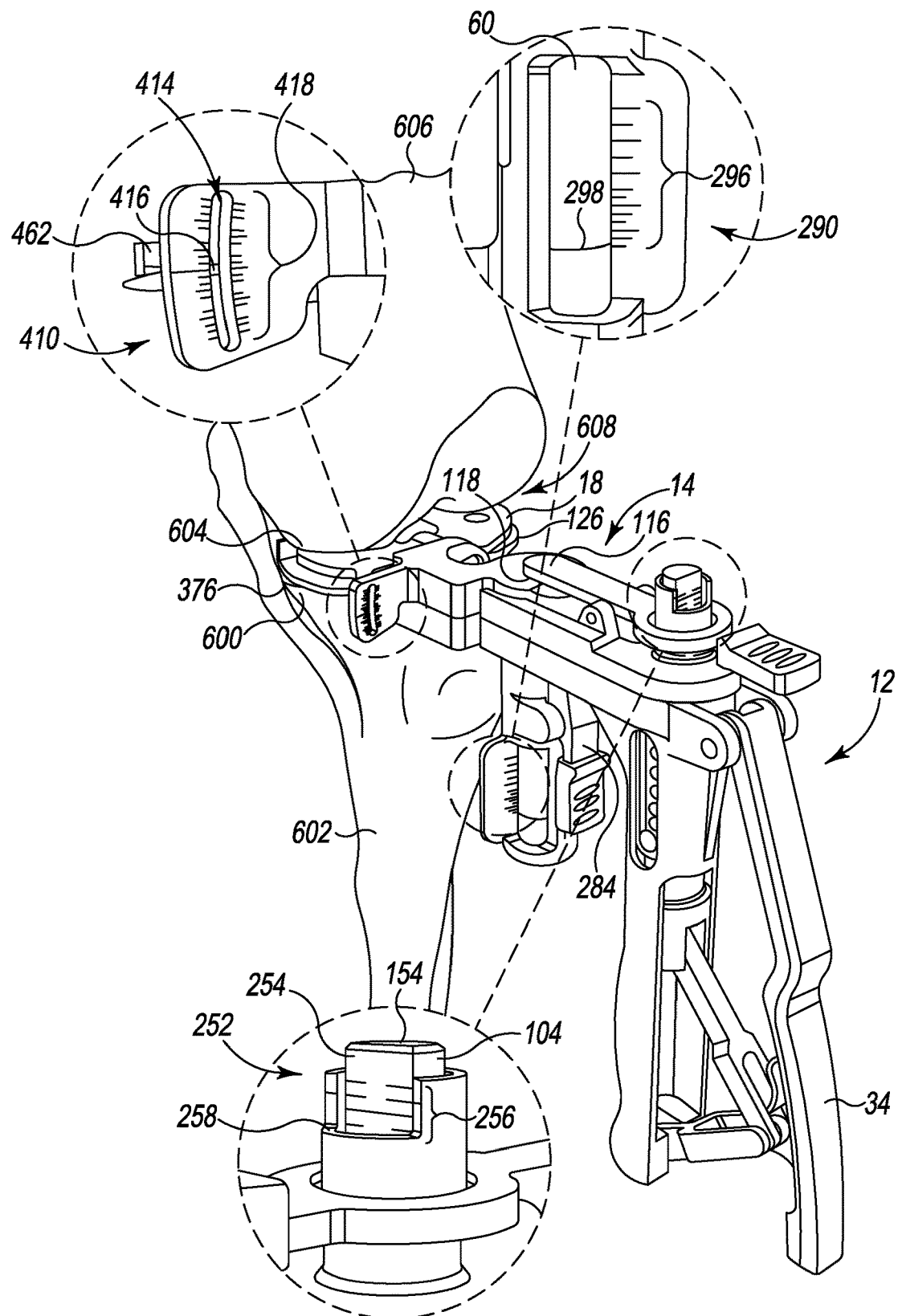
FIG. 16 is a perspective view of the balancer instrument and the distraction instrument of FIG. 2 positioned between a femur and a tibia of a patient's knee joint.

The surgeon may resect the proximal end 600 of the patient's tibia 602 to create the resected proximal surface 376 shown in FIG. 16. Prior to making any resections on the distal end 604 of the patient's femur 606, the surgeon may assess the ligaments and other soft tissues through the range of motion. To do so, the surgeon may insert the assembled balancer instrument 14 into the extension gap 608 defined between the femur 606 and tibia 602, with the tibial paddle 16 rests on the resected surface 376. As shown in FIG. 16, the femoral paddle 18 may be in a lowered or closed position relative to the tibial paddle when first inserted into the extension gap 608.

To attach the distraction instrument 12 to the balancer 14, the surgeon may align the stationary arm 30 and the moveable arm 32 with the anterior flanges 48, 88, respectively, of the balancer instrument 14. The arms 30, 32 may then be advanced over the flanges 48, 88 such that the flanges 48, 88 are received in the channels 46, 86, respectively, of the arms 30, 32. Additionally, the clip 116 of the distraction instrument 12 is advanced into the slot 118 of the balancer 14 to secure the distraction instrument 12 to the balancer instrument 14.

With the balancer 14 assembled to the distraction instrument 12 as shown in FIG. 16, the surgeon may squeeze the lever 34 to move the femoral paddle 18 away from the tibial paddle 16 and evaluate the thickness of a possible tibial insert component. The surgeon may utilize the gauge 290, noting which line 296 is aligned with the line 298 on the elongated post 60 to identify the inferior-superior distance traveled by the paddle 18 and hence the possible thickness. In that way, the surgeon evaluates the movement of the upper balancer body relative to the lower balancer body to determine the inferior-superior distance moved by the paddle.

The surgeon may also utilize the rotation gauge 410 to evaluate the amount of rotation (i.e., angle or tilt) of the femur 606 relative to the tibia 602. To do so, the surgeon monitors how the tab 416 of the femoral paddle 16 moves along the curved slot 414, noting which line 418 is aligned with the tab 416 to determine the amount of rotation. In that way, the surgeon evaluates how much the femoral paddle 16 has tilted relative to the upper balancer body to determine the degree of rotation or tilt of the femur relative to the tibia.

The surgeon may also utilize the tension gauge 252 to evaluate collateral ligament tension and balance the joint. In particular, the surgeon may apply a force to the lever 34 to move the femoral paddle 16 into contact with the patient's femur thereby separating it from the tibia which causes the ligaments of the patient's knee to exert a force back through the linkage of the instrument and displayed on the gauge 252. More specifically, the surgeon may apply sufficient force to the lever 34 to advance the elongated shaft 154 outward from the post 104. The surgeon may then note which line 256 is aligned with the surface 258 or other marking on the post 104 to determine the amount of force applied, and thereby determine ligament tension. Tension is maintained by the engagement between the tab 286 of the lever 284 and the teeth 288 of the elongated post 60. The surgeon may release the tension by operating the lever 284 of the balancer 14 to disengage the tab 286 from the teeth 288. The surgeon may then repeat each of these activities at different degrees of flexion (e.g., 0, 10, 15, and 90 degrees of flexion).

Figure 17:
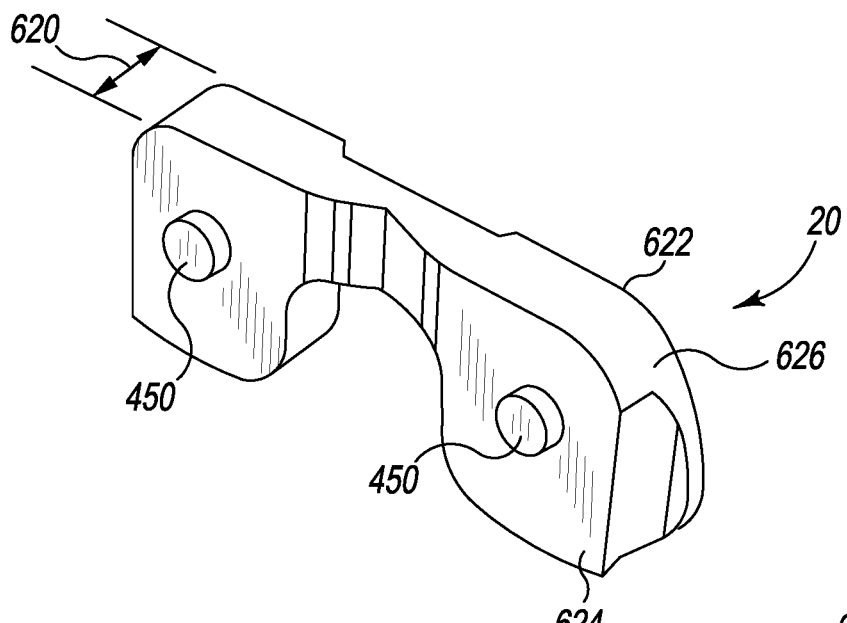
FIG. 17 is a perspective view of a femoral shim of the orthopaedic instrument system of FIG. 1.

Referring now to FIG. 17, the surgeon may select a shim 20 based on the possible tibial insert component thicknesses identified at the various degrees of flexion. Each shim 20 may have a different thickness 620 defined between its proximal surface 622 and its distal surface 624. The shim 20 includes a body 626 sized to be positioned on a femoral paddle 18, and each shim may be larger or smaller to fit on a corresponding paddle 18. A pair of posts 450 extend from a distal surface 624 of the body 626. As described above, each of the posts 450 is sized to be received in the openings 448 defined in the femoral paddle 18.

Figure 18:
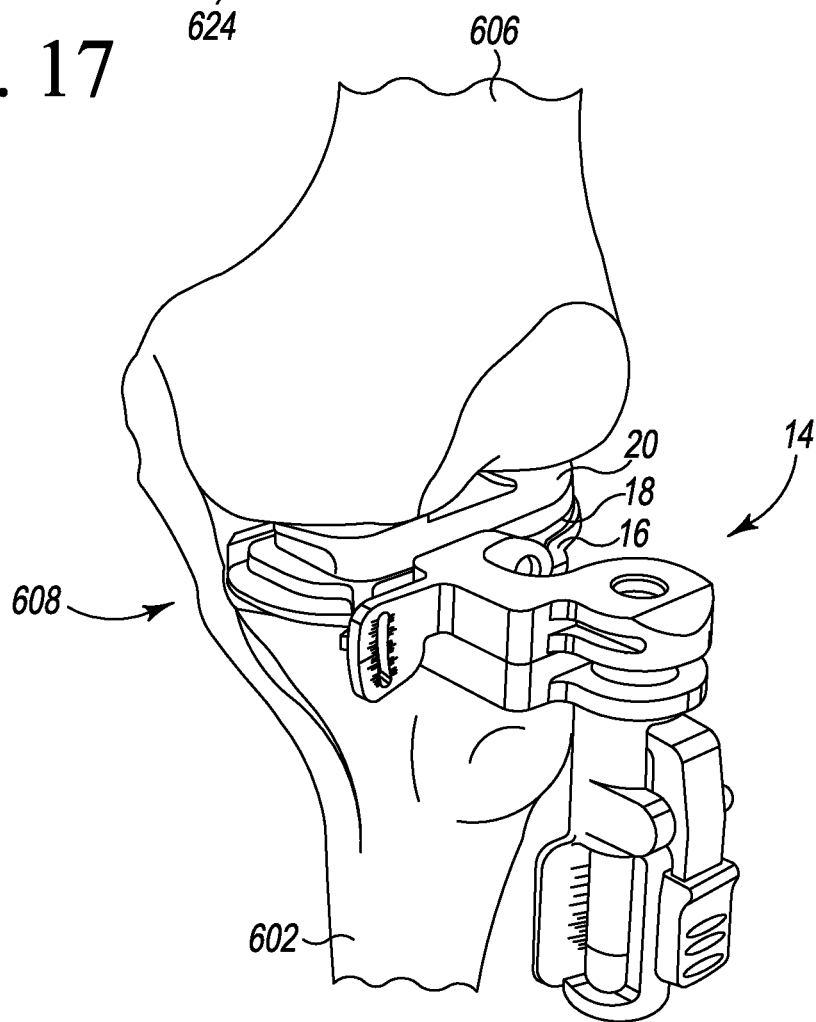
FIG. 18 is a perspective view of the balancer instrument of FIG. 2 positioned between a femur and a tibia of a patient's knee joint.

When the shim is selected, it may be attached to the balancer instrument 14 and the assembly may be inserted into the extension gap 608, as shown in FIG. 18. The surgeon may then reattach the distraction instrument 12 and repeat some of the steps outlined above to utilize the gauges 252, 290, 410 to evaluate insert thickness, femoral rotation, and ligament tension with the shim attached to the balancer instrument 14.

Figure 19:
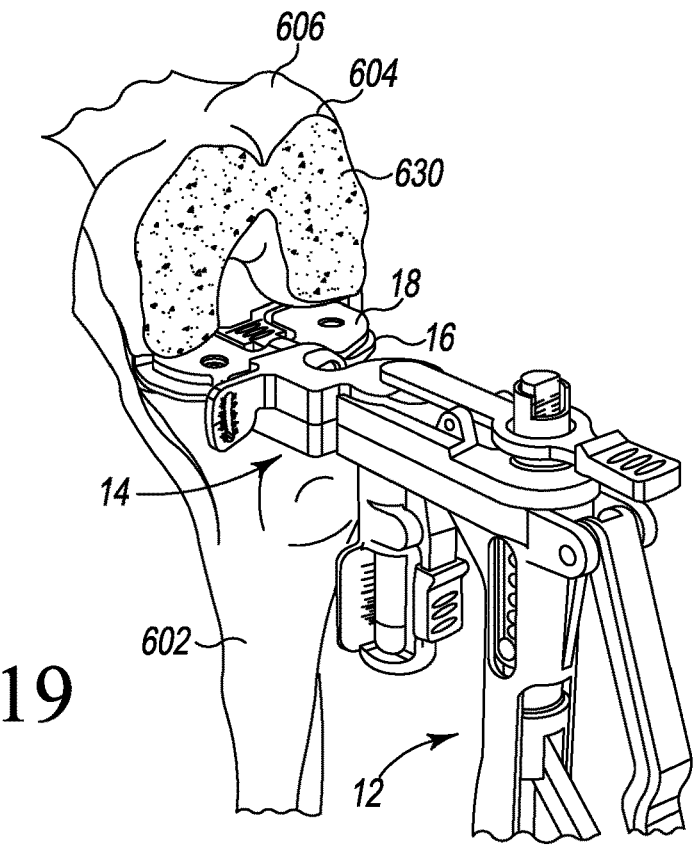
FIG. 19 is a perspective view of the balancer instrument and the distraction instrument of FIG. 2 positioned between a resected femur and a resected tibia of a patient's knee joint with the patient's knee in flexion.

Referring now to FIG. 19, the surgeon may remove the instruments 12, 14 from the patient's bone prior to resecting the distal end 604 of the femur 606 to create distal resected surface 630. With the knee in full flexion (i.e., 90 degrees), the surgeon may insert the balancer instrument 14 into the gap 632 defined between the femur 606 and tibia 602. The surgeon may also reattach the distraction instrument 12 and again repeat some of the steps outlined above to utilize the gauges 252, 290, 410 to evaluate insert thickness, femoral rotation, and ligament tension with the knee at full flexion.

Figure 20:
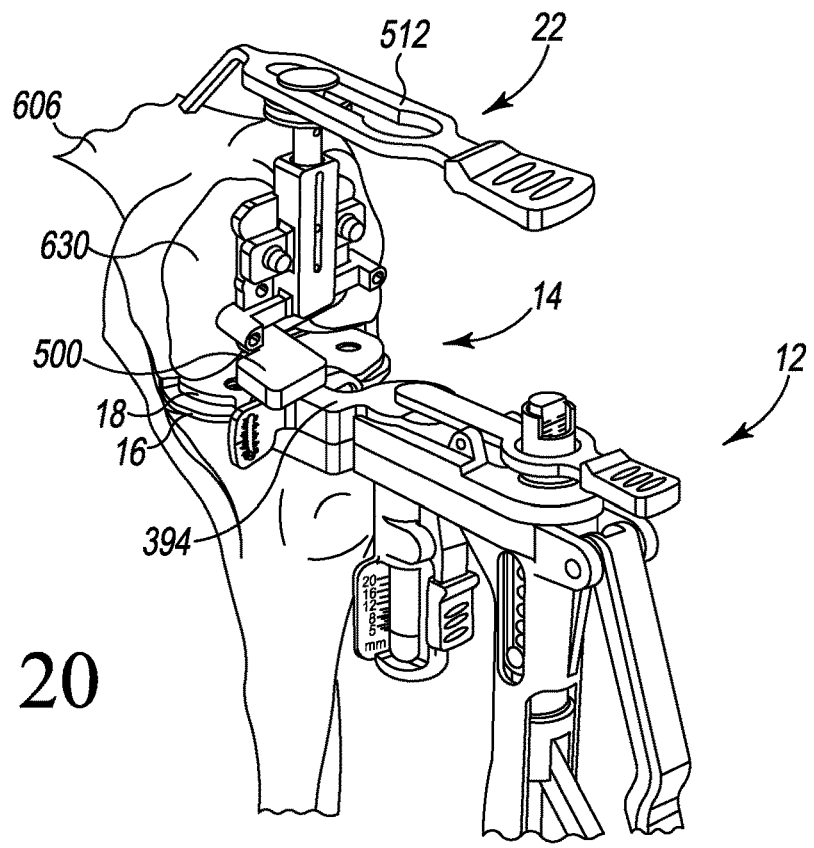
FIG. 20 is a perspective view of the orthopaedic surgical instrument system of FIG. 1 positioned between a resected femur and a resected tibia of a patient's knee joint with the patient's knee in flexion.
Figure 21:
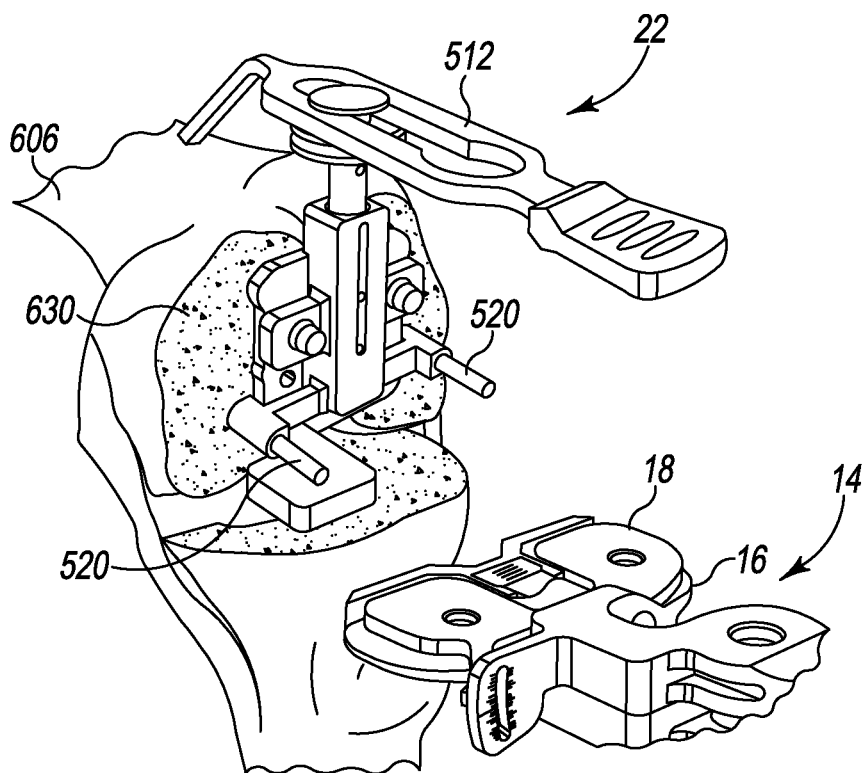
FIG. 21 is a perspective view of the femoral sizing instrument of the orthopaedic surgical instrument system of FIG. 1 positioned on the patient's resected femur.
Figure 22:
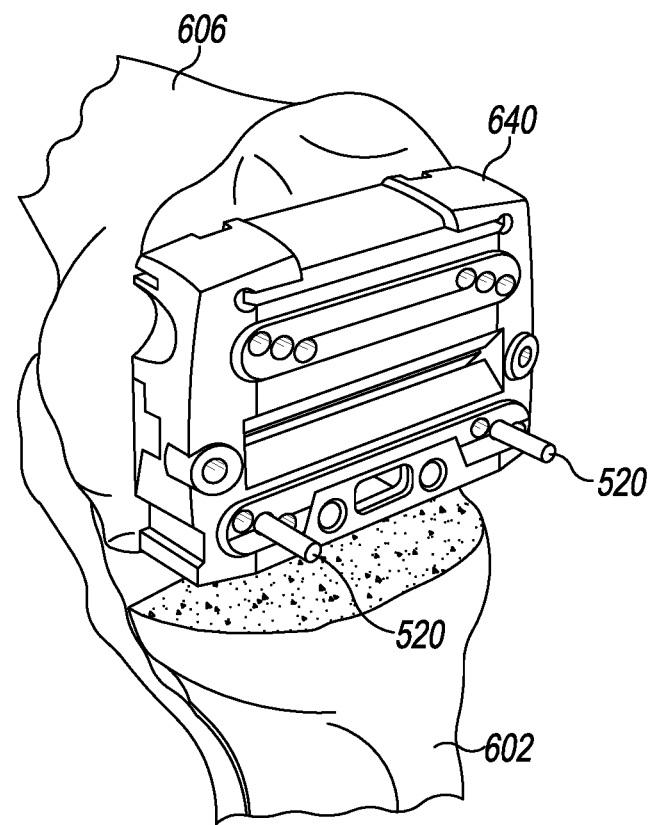
FIG. 22 is a perspective view of a cutting block of the orthopaedic instrument system.

Referring now to FIGS. 20-21, the surgeon may attach the sizing instrument 22 to the balancer instrument 14. In the illustrative embodiment, the surgeon engages the plate 504 of the instrument 22 with the distal resected surface 630 of the patient's femur 606. The surgeon may then adjust the superior-inferior position of the stylus 512 and the anterior-posterior position of the stylus 512 to indicate the proper femoral component size. As shown in FIG. 21, a surgeon may advance fixation pins 520 through guides 516 of the sizing instrument 22 and into the patient's femur 606 before removing the sizer 22 from the patient's bone. As shown in FIG. 22, the surgeon may attach a standard 4-in-1 cutting block 640 to make additional resection and prepare the patient's bones to receive the selected prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument, comprising:
  a first component including a passageway that extends along a longitudinal axis, the first component having a housing through which the passageway extends and a support arm that extends posteriorly from a superior end of the housing to a posterior end, the support arm having a first channel including a first lateral opening,
  a first plate removably coupled to the posterior end of the support arm of the first component, the first plate being shaped to be positioned on a proximal end of a patient's tibia,
  a second component including a shaft positioned in the passageway of the first component and an arm extending posteriorly from a superior end of the shaft, the arm of the second component having a second channel that includes a second lateral opening that is aligned in an anterior-posterior direction with the first lateral opening of the first channel, and
  a second plate pivotally coupled to a posterior end of the arm of the second component superior to the first plate, the second plate being configured to pivot about a pivot axis intersecting the longitudinal axis of the first component to tilt the second plate relative to the first plate,
  wherein an inferior-superior distance is defined between the second plate and the first plate, and the second component is operable to be moved along the longitudinal axis relative to the first component to change the inferior-superior distance.

2. The orthopaedic surgical instrument of claim 1, wherein the first plate includes:
  a medial pad,
  a lateral pad spaced apart from the medial pad to define a slot sized to receive the posterior end of the support arm,
  a bracket connecting the medial pad to the lateral pad, and
  a moveable flange coupled to the bracket and configured to engage the posterior end of the support arm to secure the first plate to the first component.

3. The orthopaedic surgical instrument of claim 1, wherein the first plate has a first size and is one plate of a plurality of first plates, each first plate having a size different from the first size and being configured to be selectively coupled to the support arm in place of the first plate.

4. The orthopaedic surgical instrument of claim 1, wherein:
  the posterior end of the arm of the second component includes a mounting peg, the mounting peg includes a bore that extends along the pivot axis, and
  the second plate includes a body and an elongated pin extending anteriorly from the body along the pivot axis, the elongated pin being received in the bore of the mounting peg such that the second plate is removably coupled to the arm of the second component.

5. The orthopaedic surgical instrument of claim 4, wherein the posterior end of the support arm includes a groove that is sized to receive the mounting peg of the second component.

6. The orthopaedic surgical instrument of claim 4, wherein:
the second plate includes a key extending from the body adjacent to the elongated pin, and
the mounting peg includes a keyway sized to receive the key to couple the second plate to the second component.

7. The orthopaedic surgical instrument of claim 4, wherein:
the second plate includes a tab extending from the body, and
the second component includes a flange that extends laterally from the posterior end of the arm, the flange including a plurality of visual indicia to indicate a degree of tilt of the second plate relative to the first component based on an orientation of the tab relative to the flange.

8. The orthopaedic surgical instrument of claim 1, wherein the second plate has a first size and is one plate of a plurality of second plates, each first plate having a size different from the first size and being configured to be selectively coupled to the arm of the second component in place of the first plate.

9. The orthopaedic surgical instrument of claim 1, wherein:
the second component includes a plurality of teeth on the shaft, and
the first component includes a locking arm having a head configured to engage the plurality of teeth to lock the second component in a position along the longitudinal axis, the locking arm being configured to pivot relative to the shaft to selectively engage the plurality of locking teeth.

10. An orthopaedic surgical instrument, comprising:
a first component including a passageway that extends along a longitudinal axis,
a first plate coupled to a superior end of the first component, the first plate being shaped to be positioned on a proximal end of a patient's tibia,
a second component including a shaft positioned in the passageway of the first component and an arm extending posteriorly from a superior end of the shaft,
a second plate pivotally coupled to a posterior end of the arm of the second component superior to the first plate, the second plate being configured to pivot about a pivot axis intersecting the longitudinal axis of the first component to tilt the second plate relative to the first plate, wherein an inferior-superior distance is defined between the second plate and the first plate, and the second component is operable to be moved along the longitudinal axis relative to the first component to change the inferior-superior distance, and
a third component coupled to the first component and the second component and being operable to move the second component relative to the first component, the third component including a handle that is positioned anterior of the first and second components, the handle extending along a longitudinal axis extending transverse to the pivot axis.

11. The orthopaedic surgical instrument of claim 10, wherein the third component includes:
a first distractor arm extending posteriorly from the handle, the first distractor arm being attached to the superior end of the first component,
a second distractor arm that is positioned superior of the first distractor arm, the second distractor arm being attached to the superior end of the shaft of the second component and configured to move the second component, and
a piston including an inferior end that is positioned in the handle and a superior end that is coupled to the second distractor arm, the piston being moveable relative to the handle to move the second distractor arm relative to the first distractor arm to change the inferior-superior distance defined between the first plate and the second plate.

12. The orthopaedic surgical instrument of claim 11, wherein the third component includes a lever coupled to the piston and the handle, the lever being configured to pivot relative to the handle to move the piston relative to the handle from a first position at which the inferior-superior distance is a first distance to a second position at which the inferior-superior distance is a second distance greater than the first distance.

13. The orthopaedic surgical instrument of claim 12, wherein the third component further includes:
a body including the second distractor arm, and
a biasing element positioned between a distal surface of the body and a proximal surface of the piston, the biasing element being operable to bias the piston a first distance from the second distractor arm.

14. The orthopaedic surgical instrument of claim 11, wherein the piston is moveable along an axis extending parallel to the longitudinal axis of the first component.

15. The orthopaedic surgical instrument of claim 11, further comprising a stylus coupled to the arm of the second component.

16. An orthopaedic surgical instrument system, comprising:
a first orthopaedic surgical instrument including a tibial plate and a femoral plate configured to (i) move relative to the tibial plate along an inferior-superior axis to change an inferior-superior distance, and (ii) tilt relative to the tibial plate about a pivot axis extending traverse to the inferior-superior axis, and
a second orthopaedic surgical instrument including (i) a pair of distractor arms that are configured to be coupled to the first orthopaedic surgical instrument, (ii) a handle extending along a longitudinal axis extending parallel to the inferior-superior axis, and (iii) a piston including an inferior end that is positioned in the handle and a superior end that is coupled to the second distractor arm, the piston being moveable relative to the handle to move a second distractor arm of the pair of distractor arms relative to a first distractor arm to move the femoral plate relative to the tibial plate along the inferior-superior axis.

17. The orthopaedic surgical instrument system of claim 16, wherein the second orthopaedic surgical instrument further includes:
a body including the second distractor arm, and
a biasing element positioned between a distal surface of the body and a proximal surface of the piston, the biasing element being operable to bias the piston a first distance from the second distractor arm.

18. The orthopaedic surgical instrument system of claim 16, further comprising a stylus configured to be coupled to the first orthopaedic surgical instrument.

* * * * *